(12) United States Patent  
Story et al.

(10) Patent No.: US 12,007,313 B2  
(45) Date of Patent: Jun. 11, 2024

(54) DATA FUSION TECHNIQUE FOR PREDICTING SOIL CLASSIFICATION

(71) Applicant: Southern Methodist University, Dallas, TX (US)

(72) Inventors: Brett Story, Rockwall, TX (US); Jase Sitton, Dallas, TX (US); Adam De Jong, Swanzey, NH (US)

(73) Assignee: SOUTHERN METHODIST UNIVERSITY, Dallas, TX (US)

( * ) Notice: Subject to any disclaimer, the term of this patent is extended or adjusted under 35 U.S.C. 154(b) by 1520 days.

(21) Appl. No.: 15/977,886

(22) Filed: May 11, 2018

(65) Prior Publication Data

US 2018/0333894 A1 Nov. 22, 2018

Related U.S. Application Data

(60) Provisional application No. 62/507,677, filed on May 17, 2017.

(51) Int. Cl.
| | |
|---|---|
| *G01N 1/04* | (2006.01) |
| *C04B 14/36* | (2006.01) |
| *C04B 28/04* | (2006.01) |
| *E04B 1/00* | (2006.01) |
| *E04B 2/18* | (2006.01) |
| *E04C 1/00* | (2006.01) |

(Continued)

(52) U.S. Cl.
CPC .............. *G01N 1/04* (2013.01); *C04B 14/361* (2013.01); *C04B 28/04* (2013.01); *E04B 2/18* (2013.01); *E04C 1/00* (2013.01); *G01N 33/24* (2013.01); *G01N 3/08* (2013.01); *G01N 3/20* (2013.01); *G01N 2203/0003* (2013.01); *G01N 2203/0019* (2013.01); *G01N 2203/0023* (2013.01); *G01N 2203/0067* (2013.01)

(58) Field of Classification Search
CPC ................................. G01N 33/24; G01N 3/08
See application file for complete search history.

(56) References Cited

U.S. PATENT DOCUMENTS 7,130,834 B2 * 10/2006 Anderson ............. G06N 3/045  
706/15  
2003/0023386 A1 * 1/2003 Aranibar ............... G16B 40/30  
702/19

FOREIGN PATENT DOCUMENTS

IN 4308/MUM/2015 A * 5/2017  
WO WO 2015/156541 * 10/2015

OTHER PUBLICATIONS

Sitton et al. Estimating soil classification via quantitative and qualitative field testing for use in constructing compressed earth blocks , Apr. 2016.*

(Continued)

*Primary Examiner* — Mohamed Charioui  
*Assistant Examiner* — Lynda Dinh  
(74) *Attorney, Agent, or Firm* — Edwin S. Flores; Daniel J. Chalker; Chalker Flores, LLP

(57) ABSTRACT

Provided herein is a method for determining a soil classification comprising: obtaining a soil sample; conducting two or more field tests on the soil sample to obtain raw data for each field test; and calculating the soil classification from the raw data by applying a previously obtained validation dataset obtained from a training and validation soil classification calculation using samples of known soil classification, wherein the validation dataset is obtained using a feed-forward backpropagation neural network.

12 Claims, 14 Drawing Sheets

$$a = f\left(\sum_{j=1}^{5} w_{i,j} x_j + b\right)$$

(51) Int. Cl.
G01N 3/08 (2006.01)
G01N 3/20 (2006.01)
G01N 33/24 (2006.01)

(56) References Cited

OTHER PUBLICATIONS

Holtz et al. Materials Soil classification, 2004.*
Bhattacharya et al. Machine learning in soil classification, 2006.*
Yudong. Soil classification by neural network. 1994.*
Han et al. Classification. 2012.*
US Army. Materials Testing. 2015.*
Soil-net.com/Soil under microscope.*
Adam, E., et al., "Compressed Stabilised Earth Block Manufacture in Sudan," Paris, France Jul. 2001, http://unesdoc.unesco.org/images/0012/001282/128236e.pdf.
Adeli, H., "Neural networks in civil engineering: 1989-2000," Comput. Civ. Infrastruct. Eng. 16 (2001), pp. 126-142.
Allen, G.T.R., "Strength Properties of Stabilized Compressed Earth Blocks with Varying Soil Compositions," University of Colorado, Boulder, Jul. 26, 2012, 108 pp.
ASTM Designation: D 2487-00, "Standard Practice for Classification of Soils for Engineering Purposes (USCS)," American Society for Testing and Materials, 2011, pp. 246-257.
ASTM Designation: D 4318-00, "Standard Test Methods for Liquid Limit, Plastic Limit, and Plasticity Index of Soils," American Society for Testing and Materials, 2010, pp. 561-574.
ASTM Designation: D 422 (hydrometer), "Standard Test Methods for Particle—Size Analysis of Soil," American Society for Testing and Materials, 2007, 15 pp.
Aubert, J. E., et al., "Chequered earth construction in south-western France," J. Cult. Herit., Aug. 18, 2014, 16 (2015) 293-298.
Bachar, M., et al., "Characterization of a stabilized earth concrete and the effect of incorporation of aggregates of cork on its thermo-mechanical properties: Experimental study and modeling," Constr. Build. Mater., Sep. 2014, vol. 74 (2015) 259-267.
Bhargavi, P., et al., "Applying Naive Bayes data mining technique for classification of agricultural land soils," Int. J. Comput. Sci. Netw. Secur., vol. 9, No. 8, Aug. 2009, pp. 117-122.
Bhargavi, P., et al., "Soil Classification Using Gatree," Int. J. Comput. Sci. Inf. Technol. vol. 2, No. 5, Oct. 2010, pp. 184-191.
Dahmen, J., et al., "Earth Masonry Unit: Sustainable CMU Alternative," GEOMATE-Nagoya, Nov. 13-15, 2013, 7 pp.
Delgado, M. Carmen Jimenez, et al., "The Selection of Soils for Unstablilized Earth Buildilng: A Normative Review," Construction and Building Materials, Aug. 2005, 16 pp.
https://dwellearth.com/soil-science-2/, 2016, last accessed Sep. 19, 2018, 6 pp.
Egenti, C., et al., "Conceptualisation and pilot study of shelled compressed earth block for sustainable housing in Nigeria," International Journal of Sustainable Built Environment, May 2014, vol. 3, pp. 72-86.
Grunert, Brett Ryan, Thesis, "The Development of a Standard of Care Defining Suitable Testing of Geomaterials Intended for Unstablilized Compressed Earth Block Construction," University of Colorado, Boulder, ProQuest, LLC, 2009, 195 pp.
Guillaud, H., et al., "Compressed Earth Blocks: Manual of Design and Construction," vol. II, 1995, 192 pp.
Haykin, S., "Neural Networks: A Comprehensive Foundation," Macmillan College Publishing Company, Englewood Cliffs, NJ, 1994, Chapter 6, "Multilayer Perceptrons," 20 pp.
Hornik, K., et al., "Multilayer Feedforward Networks are Universal Approximators," Neural Networks, 2, 1989, pp. 359-366.
Kaniu, M.I., et al., "Challenges in rapid soil quality assessment and opportunities presented by multivariate chemometric energy dispersive X-ray fluorescence and scattering spectroscopy," Geoderma 241-242, Oct. 2014, pp. 32-40.
Krosnowski, A.D., "A Proposed Best Practice Method of Defining a Standard of Care for Stabilized Compressed Earthen Block Production," Theses for University of Colorado, Boulder, Apr. 2011, 101 pp.
Morel, J.C., et al., Compressive strength testing of compressed earth blocks, Constr. Build. Mater. 21, 2007, pp. 303-309.
Morony, J.J., Adobe Moisture Absorption and Temperature Control, Logged Data for a Humid Heat Waive, Aug. 6-11, Del Rio, TX, 2005, 7 pp.
Rigassi, V., "Compressed Earth Blocks: Manual of Production, vol. I," Vieweg, Eschborn, Germany, 1985, 143 pp.
Riza, F., et al., "A Brief Review of Compressed Stabilized Earth Brick (CSEB)," 2010 International Conference on Science and Social Research (CSSR 2010), Dec. 5-7, 2010, Kuala Lumpur, Malaysia, 6 pp.
Story, B., et al., "Methodology for Designing Diagnostic Data Streams for Use in a Structural Impairment Detection System," J. Bridge Eng., May 19, 2014, 19(4), pp. 04013020-1 to 040103020-11.
Story, B., et al., "A Structural Impairment Detection System Using Competitive Arrays of Artificial Neural Networks," Computer-Aided Civil and Infrastructure Engineering, vol. 29, 2014, pp. 180-190.
Zeinali, Y., et al., "Structural Impairment Detection Using Deep Counter Propagation Neural Networks," International Conference on Sustainable Design, Engineering and Constructions, Procedia Engineering, vol. 145, 2016, pp. 868-875.
Zeinali, Y., et al., "Competitive probabilistic neural network," Integrated Computer-Aided Engineering, vol. 1, Jan. 2017, pp. 1-14.

* cited by examiner

Figure 4.1: 3-point bending test setup

DATA FUSION TECHNIQUE FOR PREDICTING SOIL CLASSIFICATION

CROSS-REFERENCE TO RELATED APPLICATIONS

This application claims priority based on U.S. Provisional Application No. 62/507,677, filed May 17, 2017. The contents of which is incorporated by reference in its entirety.

TECHNICAL FIELD OF THE INVENTION

The present invention relates in general to the field of soil classification, and more particularly, to a novel data fusion technique for predicting soil classification.

STATEMENT OF FEDERALLY FUNDED RESEARCH

None.

BACKGROUND OF THE INVENTION

Without limiting the scope of the invention, its background is described in connection with soil classification.

Compressed earth blocks (CEBs) represent a cost-effective, sustainable, and environmentally-friendly building alternative to traditional masonry elements. CEB construction uses low-cement, compressed local soil brick units that are rapidly and efficiently manufactured on site. CEB construction uses local soil as the primary component, which provides advantages over traditional masonry elements including lower cost, increased energy efficiency, and lower environmental impact [1-13].

One significant challenge with prolific CEB construction is the lack of standardization in the United States and internationally [2,6,8,12]. The United States, France, New Zealand, and different parts of Africa have standards that address soil selection and CEB construction, however they vary widely in their recommendations. Some of these standards address the qualities of the soil found through laboratory or field soil analysis, while others rely on the strength of the cured block to determine suitability for construction.

The ultimate behavior (e.g. structural resistance, energy efficiency, constructability) of a CEB structure is dependent on properties of the character of soil, which vary based on location [1,2,4-8,10-12,14,15]. Soil classification standards such as the Unified Soil Classification System (USCS) and the American Association of State Highway and Transportation Officials (AASHTO) require laboratory testing; therefore, standardized assessment of soil characteristics in the field may be difficult. Typically, field tests provide primarily qualitative data collected by builders of varying experience; some quantitative data can also be collected [8,10].

Thus, a need remains for a robust, easy method for determining soil classification in the field without the use of expensive and complex laboratory equipment.

SUMMARY OF THE INVENTION

In one embodiment, the present invention includes a method of determining a soil classification comprising: obtaining a soil sample; conducting two or more field tests on the soil sample to obtain raw data for each field test; and calculating the soil classification from the raw data obtained in the field by applying a previously obtained validation dataset obtained from a training and validation soil classification calculation using known samples. In one aspect, the soil classification is determined without laboratory equipment. In another aspect, the field tests are selected from wash test, a feel test, a test tube particle graduation, or a jar test. In another aspect, the soil classification is within 10% of that obtained using laboratory testing of the soil. In another aspect, the feel test further comprises at least one of a pen test, a stick test, or a shine test. In another aspect, the method further comprises the displaying graphically the soil classification. In another aspect, the validation dataset obtained from a training and validation soil classification was determined using a feed-forward backpropagation neural network. In another aspect, the soil classification is a Unified Soil Classification System (USCS) classification. In another aspect, the method further comprises displaying the soil classification on a soil texture triangle. In another aspect, the method further comprises using the soil classification to make compressed earth blocks. In another aspect, the method further comprises training a neural network using at least two hidden layers to obtain the validation dataset that is applied to the soil sample tests. In another aspect, the method further comprises adding noise to the test samples that comprise one or more qualitative tests used to train a neural network to obtain the validation dataset that is applied to the tests of the soil samples.

In another embodiment, the present invention includes a method of making a compressed earth block (CEB) comprising: obtaining a soil sample; conducting two or more field tests on the soil sample, wherein the field tests provide raw data for each test without the use of a laboratory; calculating the soil classification from the raw data obtained in the field by applying a previously obtained validation dataset obtained from a training and validation soil classification calculation using known samples; and mixing a local soil, water, and a stabilizer into a CEB based on the calculated soil classification from the soil sample. In one aspect, the field test are two or more field tests that are selected from wash test, a feel test, a test tube particle graduation, or a jar test, to obtain raw data for each test. In another aspect, the feel test further comprises at least one of a pen test, a stick test, or a shine test. In another aspect, the soil classification is within 10% of that obtained using laboratory testing of the soil. In another aspect, the method further comprises displaying graphically the soil classification. In another aspect, the validation dataset obtained from a training and validation soil classification was determined using a feed-forward backpropagation neural network. In another aspect, the soil classification is a Unified Soil Classification System (USCS) classification. In another aspect, the method further comprises displaying the soil classification on a soil texture triangle. In another aspect, the method further comprises using the soil classification to make compressed earth blocks. In another aspect, the method further comprises training a neural network using at least two hidden layers to obtain the validation dataset that is applied to the soil sample tests. In another aspect, the method further comprises adding noise to the test samples that comprise one or more qualitative tests used to train a neural network to obtain the validation dataset that is applied to the tests of the soil samples. In another aspect, the method further comprises adjusting the ratio of the local soil, the water, and the stabilizer to reach a pre-determined CEB performance.

In yet another embodiment, the present invention includes a compressed earth block made by a method comprising: mixing a local soil, water, and a stabilizer into a CEB based on a calculated soil classification from the local soil sample, wherein the calculated soil classification from the soil sample is determined by: conducting two or more of the following tests in the field on the local soil sample, wherein the tests are selected from wash test, a feel test, a test tube particle graduation, or a jar test, to obtain raw data for each test; and calculating the soil classification from the raw data obtained in the field by applying a previously obtained validation dataset obtained from a training and validation soil classification calculation using known samples. In one aspect, the soil classification is determined without laboratory equipment. In another aspect, the soil classification is within 10% of that obtained using laboratory testing of the soil. In another aspect, the feel test further comprises at least one of a pen test, a stick test, or a shine test.

In another embodiment, the present invention includes a computerized method for determining a soil classification, the method comprising: acquiring a dataset from two or more of the following tests in the field, wherein the tests are selected from wash test, a feel test, a test tube particle graduation, or a jar test, to obtain raw data for each test; and using a processor to train a neural network using at least two hidden layers to obtain the validation dataset that is applied to the soil sample tests; calculating the soil classification from the raw data obtained in the field by applying a previously obtained validation dataset obtained from a training and validation soil classification calculation using known samples; and storing or displaying the soil classification. In one aspect, the processor is in a smartphone, tablet, handheld device, computer, on a global telecommunications network, or in the cloud.

In another embodiment, the present invention includes a system for determining a soil classification, the system comprising: acquiring a dataset from two or more of the following tests in the field, wherein the tests are selected from wash test, a feel test, a test tube particle graduation, or a jar test, to obtain raw data for each test; a processor comprising a non-transitory computer readable medium comprising instructions stored thereon for: calculating the soil classification from the raw data obtained in the field by applying a previously obtained validation dataset obtained from a training and validation soil classification calculation using known samples; and storing or displaying the soil classification. In another aspect, the system further comprises using a processor to train a neural network using at least two hidden layers to obtain the validation dataset that is applied to the soil sample tests.

In another embodiment, the present invention includes a method for designing a mix for making a compressed earth block (CEB) comprising: identifying a soil classification for a local soil with a neural network; selecting a desired brick strength; and modifying the local soil with a soil additive to prepare a mix for making the compressed earth block brick. In one aspect, the mix is modified according to FIG. 4 to modify the local soil to a predetermined soil composition. In another aspect, the soil additive selected from at least one of: a sand, a cement, a clay, a water, a polymer, a lime, a fly ash, or a soil amendment. In another aspect, the method further comprises conducting a neural network analysis for the soil additive added to the soil classification to optimize the strength of the compressed earth block.

In yet another embodiment, the present invention includes a compressed earth block made by a method comprising: identifying a soil classification for a local soil with a neural network; selecting a desired brick strength; and modifying the local soil with a soil additive to prepare a mix for making the compressed earth block brick to make a modified soil with a predetermined soil composition; and mixing the modified soil with water and cement to form the compressed earth brick having the desired strength. In one aspect, mix is modified according to FIG. 4 to modify the local soil to a predetermined soil composition. In another aspect, the soil additive selected from at least one of: a sand, a cement, a clay, a water, a polymer, a lime, a fly ash, or a soil amendment. In another aspect, the method further comprises conducting a neural network analysis for the soil additive added to the soil classification to optimize the strength of the compressed earth block.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
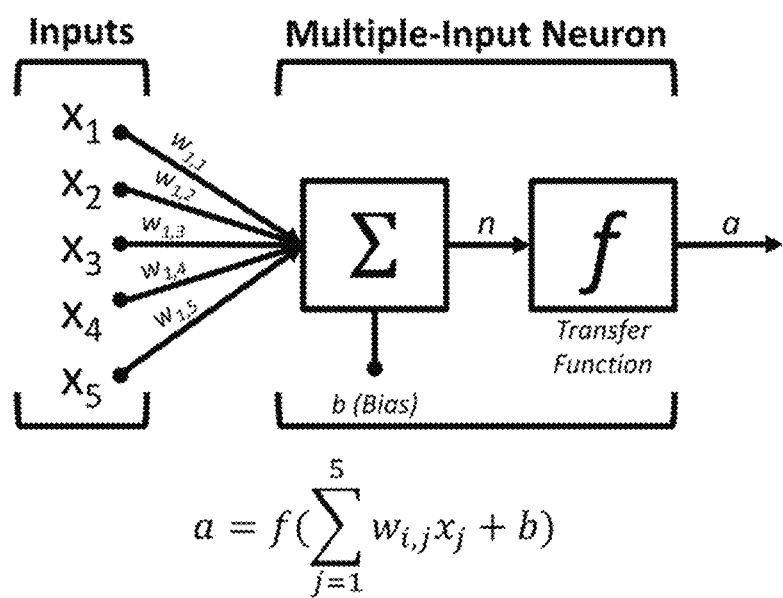
FIG. 1 shows a multiple-input neuron diagram.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Abbreviations: CEB, compressed earth block; ANN, artificial neural network; USCS, Unified Soil Classification System; ASTM, American Society of Testing and Materials.

As used herein, the terms "Compressed earth blocks (CEBs)", "pressed earth block" or a "compressed soil block", refer to traditional masonry elements, which represent a cost-effective, sustainable, and environmentally-friendly building alternative to traditional masonry elements. CEB construction comprises low-cement, compressed local soil brick units that are rapidly and efficiently manufactured on-site. CEB construction uses local soil as the primary component, which provides advantages over traditional masonry elements including lower cost, increased energy efficiency, and lower environmental impact.

Typically, CEBs are assembled in walls using standard bricklaying and masonry training, techniques, and equipment known to the skilled bricklayer/masonry worker. The mortar between the CEBs is generally made from a simple slurry of the same soil/clay mix (often without aggregate). The mortal is spread, applied, or brushed very thinly between the CEBs for bonding. For higher strength, cement mortar may be used. Cement mortar is also used is building in areas with freeze-thaw cycles. The CEBs can also be shaped to be interlocking.

One significant challenge with prolific CEB construction is the lack of standardization in the United States and internationally. The United States, France, New Zealand, and different parts of Africa have standards that address soil selection and CEB construction; however, they vary widely in their recommendations. Some of these standards address the qualities of the soil found through laboratory or field soil analysis, while others rely on the strength of the cured block to determine suitability for construction. Thus, the present invention can be used in any area of the world and the neural network process applied to local standards and soil, independent of the classification system used in other countries or regions. Thus, the present invention provides a robust and reproducible way to determine the soil classification at the local level, with little or no equipment, with results customized to the local soil, available materials, a conditions (e.g., type of soil, type of aggregate, or humidity).

The ultimate behavior (e.g., structural resistance, energy efficiency, constructability) of a CEB structure is dependent on properties of the character of soil, which vary based on location. Soil classification standards such as the Unified Soil Classification System (USCS) and the American Association of State Highway and Transportation Officials (AASHTO) require significant laboratory testing (equipment and training); therefore, standardized assessment of soil characteristics in the field may be difficult or impossible.

Typically, field tests provide primarily qualitative data collected by builders of varying experience; some quantitative data can also be collected.

Soil properties of interest in CEB construction are particle distribution, clay content, and plasticity. Particle distribution and clay content establish the makeup of a soil, but is also important to understand how a soil behaves; the plasticity of a soil establishes the behavior when water is introduced. These properties affect mix acceptability and govern the ability of the soil to form a solid brick. Laboratory procedures to characterize these soil properties are detailed in ASTM D422 and ASTM D4318 (ASTM 2007; ASTM 2010), relevant portions incorporated herein by reference. The Unified Soil Classification System (USCS) is a widely-used soil classification system that uses the aforementioned soil properties to assign a soil a classification. The USCS can be found in ASTM D2487 (ASTM 2011), relevant portions incorporated herein by reference.

The need for rapid soil classification is not limited to CEB construction. Regardless of the type of earthen construction selected (e.g. extruded bricks, adobe, rammed earth, and wattle and daub), it is apparent that understanding the quality of soil at a site is crucial to successful earthen construction. Obtaining a soil's classification through USCS requires specialized equipment and laboratory space, which are rarely available in remote locations or developing areas. Current efforts in rapid soil classification focus on the use of spectroscopy or spectrometry, which require specialized equipment, intensive analysis, and extensive training and calibration.

An alternative to more expensive and specialized analysis methods is manual field soil analysis, which includes rapid tests performed with simple tools on-site. These tests are designed so that builders can quickly estimate soil properties to determine soil acceptability for CEB unit construction; these data have not been used to obtain rigorous, ASTM quality scientific measurements as tests yield qualitative and quantitative data that maybe subjective or imprecise. The primary challenge in rapid soil classification in field conditions is the collection and analysis of data that can accurately and efficiently determine critical soil parameters and, subsequently, a classification.

The present invention includes the development of an artificial neural network framework that provides qualitative and quantitative field soil analyses to standardized laboratory soil analyses and, ultimately, USCS classification. Neural networks are an appropriate alternative to deterministic methods when the input-output relationship is intractable or difficult to implement. Neural networks can also be trained to be fault-tolerant, robust classifiers that are capable of utilizing all data, quantitative and qualitative, to make an assessment. The present invention fuses neural networks with qualitative and quantitative field assessment data to establish a relationship between field data and USCS soil classifications, which has the advantage of the speed of field soil analysis while still providing useful information about the soil.

The relationship between the field soil analysis test results currently used to judge a soil's suitability for CEB production and ASTM standardized laboratory soil analysis results is difficult to represent deterministically. This is in large part due to the qualitative nature of the majority of the field soil analysis tests. The present inventors developed a novel artificial neural network (ANN) to solve the problem of judging the suitability of a soil for CEB production and ASTM standardized laboratory soil analysis.

Neural networks can be trained to be fault-tolerant, robust classifiers that use all data, quantitative and qualitative, to make an assessment. Artificial neural networks are analytical models designed to mimic the input/output associations of the human neural structure. They are powerful pattern recognizers and classifiers and are particularly suitable for problems that are too complex to be modeled and solved by classical mathematics and traditional procedures. Neural networks are capable of modeling input-output functional relations even when mathematically explicit formulas are unavailable; this is achieved by training the networks (e.g. weight adjustment, statistical optimization) on known input/output data until the network can appropriately represent the input/output space. The present invention uses machine-learning techniques to operate on a dataset of quantitative standardized field data obtained from direct tests using specialized equipment.

Rapid Soil Classification. The need for rapid soil classification includes, but is not limited to, CEB construction. Regardless of the type of earthen construction selected (e.g. extruded bricks, adobe, rammed earth, and wattle and daub), it is apparent that understanding the quality of soil at a site is crucial to successful earthen construction [7,8,15]. For this paper and specifically CEB construction, the USCS classification system is used.

Obtaining a soil's classification through USCS requires specialized equipment and laboratory space, which are rarely available in remote locations or developing areas. Current efforts in rapid soil classification focus on the use of spectroscopy or spectrometry; these methods require specialized equipment and intensive analysis [19].

An alternative to more expensive and specialized analysis methods is manual field soil analysis, which includes quick tests performed with simple tools on site [8,10]. These tests are designed so that builders can quickly estimate soil properties to determine soil acceptability for CEB unit construction; these data have not been used to obtain rigorous, ASTM quality scientific measurements as tests yield qualitative and quantitative data that maybe subjective or imprecise. The primary challenge in rapid soil classification in field conditions is the collection and analysis of data that can accurately and efficiently determine critical soil parameters and, subsequently, a classification [19].

This paper presents an artificial neural network framework that relates the results of qualitative and quantitative field soil analyses to standardized laboratory soil analyses and, ultimately, USCS classification. Neural networks are an appropriate alternative to deterministic methods when the input-output relationship is intractable or difficult to implement [20-22]. Neural networks can also be trained to be fault-tolerant, robust classifiers that are capable of utilizing all data, quantitative and qualitative, to make an assessment. In this paper, neural networks fuse qualitative and quantitative field assessment data and establish the relationship between field data and USCS soil classifications, which has the advantage of the speed of field soil analysis while still providing useful information about the soil.

Neural Networks. Artificial neural networks are analytical models designed to mimic the input/output associations of the human neural structure. They are powerful pattern recognizers and classifiers and are particularly suitable for problems that are too complex to be modeled and solved by classical mathematics and traditional procedures [23-26]. Neural networks are capable of modeling input-output functional relations even when mathematically explicit formulas are unavailable; this is achieved by training the networks (e.g. weight adjustment, statistical optimization) on known input/output data until the network can appropriately represent the input/output space. Others have applied Naive Bayes data mining techniques and genetic algorithms to rapidly classify soils based on field data. In this work, the machine learning techniques operate on a dataset of quantitative standardized field data obtained from direct tests using specialized equipment [27,28].

The complex, nonlinear relationship between USCS classification, Y, and diagnostic field test data streams, X, is difficult to ascertain deterministically, and neural networks are an appropriate technique for establishing this relationship. Material properties, data collection techniques, and other uncertainties contribute to difficulties in developing the relationship.

One common and effective type of neural network used in engineering applications is the feed-forward backpropagation neural network. These neural networks are made up of multiple-input neurons that are theorized to mimic the function of neurons in the brain. Neurons receive an input vector and produce an output. In feed-forward neural networks, each input in the input vector is multiplied by a unique, initially random, numerical weight. These weighted inputs are then summed and a constant bias is added to shift the output of the neuron so that constant portions of linear relationships may be captured. This value is then passed through a transfer function, which is essentially a normalization function and can take many different forms (e.g. a threshold function, piecewise-linear function, or sigmoid function) to obtain the output of the neuron [23,24]. FIG. 1 shows a diagram of a multiple-input neuron, where $x_{1 \ldots R}$ are the network inputs in the input vector, $w_{i,1 \ldots R}$ are the unique weights applied to each input, b is the constant bias added to the summation of the weighted inputs, n is the output of the neuron that is fed into the transfer function f, and a is the final output of the neuron.

Neural networks are organized into layers. The input layer and output layer contain the input data and the resulting output data. Hidden layers between the input and output layers contain the neurons and are connected by the weights; there may be any number of hidden layers, and it has been shown, theoretically, that a two-layer network may map any non-linear relationship [29]. Each layer is a vector containing any number R of neurons, and the output of that layer is a vector of length R containing the output from each neuron in that layer. This output vector is then passed as the input vector for the next hidden layer; the process repeats through all hidden layers until the final output of the network is reached.

The neural networks utilized in this paper are feed-forward backpropagation neural networks. In the case of feed-forward backpropagation, the training occurs by the adjustment of the synaptic weights. The weights are initialized as random numbers. The first pass of the training dataset are input into the network and an output is generated. If this output does not match the target within a predefined acceptable error, the weights and biases within the network are adjusted by minimizing an error function relating the simulated output and the target output.

Training is complete when the error between the simulated outputs and target outputs is sufficiently small, in an average sense, over all training and validation data.

Soil Data Collection and Classification

Figure 2:
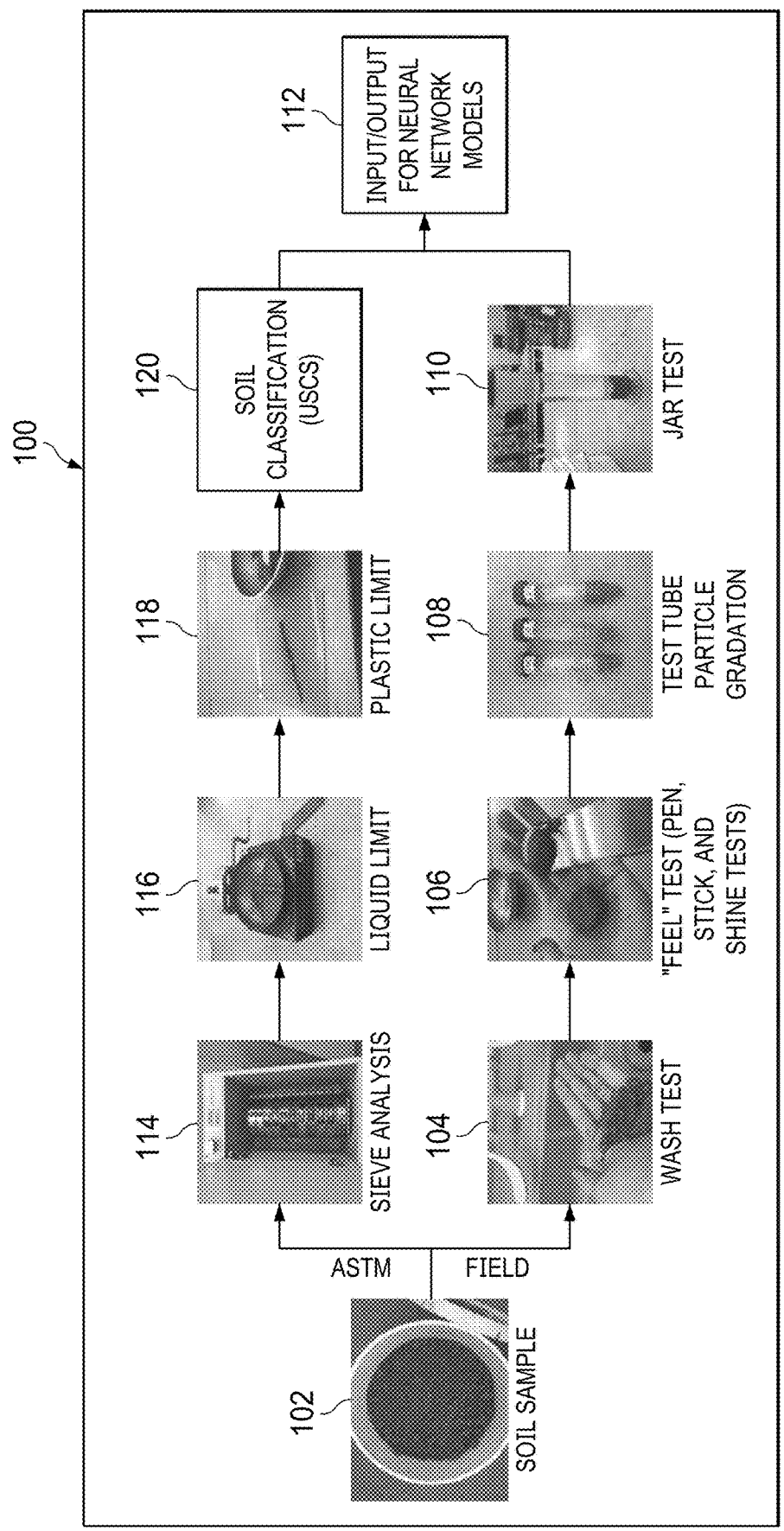
FIG. 2 shows a soil analysis flow chart of the present invention.

Neural networks require sufficient training data to appropriately map the desired input-output relationship. A training dataset was obtained by performing two distinct analyses on each soil sample: ASTM standard laboratory tests and field tests. Results from field test soil analyses are the inputs to the classification network; the desired output is the correct USCS classification for each soil as determined by ASTM tests. The flow chart 100 for this process is shown in FIG. 2. The individual steps are discussed in greater detail in subsequent sections. In step 102, a soil sample is obtained. The flowchart 100 then separates into two tracks. In step 104, a wash test is conducted with the soil sample. In step 106, any of a variety of "feel" tests are conducted, as outlined hereinbelow. In step 108, a test tube particle gradation test is conducted. In step 110, a jar test is conducted on the soil sample. The results of the same are input at step 112, through the input/output for the neural network model. The second track can be used when validating the model, including at step 114 a sieve analysis. Next, at step 116, a liquid limit analysis is conducted. At step 118, the soil is analyzed with a plastic limit test. Finally, in step 120, the soil classification (USCS) is determined from the soil sample. The skilled artisan will recognized that steps 114-120 are the standard laboratory methods used today that require expensive equipment, training and expertise to conduct the analysis to determine a soil classification. As shown herein, an equivalent determination of soil classification can be made from the same soil sample following the steps 102-112, and then applying the data obtained from steps 104-110, into the neural network model to obtain the same analysis without any expensive equipment, a laboratory, or extensive training or expertise, making the present invention easily applied in the field without the need for a laboratory.

ASTM Standardized Soil Analysis

Classification of a soil according to the USCS requires determination of three soil properties: the soil's particle gradation, the fines content (particles less than 75 μm in diameter), and the plasticity of the soil [18]. The particle gradation can be determined by performing a dry sieve analysis on the soil sample, which includes sifting the soil through a stack of wire mesh sieves of decreasing mesh size [16]. The fines content of the soil can also be determined through dry sieve analysis, however many soils contain clumps of fine particles that do not properly pass through the sieves and may distort the results. In such cases, fines content was therefore determined through wet sieve analysis, which involves using running water to wash fines through a no. 200 sieve and weighing the remainder to determine the percentage of fines [12]. The plasticity was determined by testing the soil for its liquid limit and plastic limit. The liquid limit is defined as the water content (%) of a soil at the boundary between the semi-liquid and plastic states, while the plastic limit is defined as the water content (%) of a soil at the boundary between the plastic and semi-solid states [17]. A soil exhibits plastic behavior if its water content is between the liquid and plastic limits; this range of plasticity is called the plasticity index, and is numerically defined as the difference between the liquid limit and the plastic limit. The plasticity index of a soil gives a measure of the plasticity of the soil that can be used for classification. The procedures for finding the liquid and plastic limits can be found in ASTM D4318 [17].

Field Soil Analysis

The field soil analysis tests are:
The Pen Test—Water is added to the sample until it forms a putty. The putty is rolled into a "pen" shape. If it breaks before it can reach the diameter of a pen (approximately ⅛"), the soil has low plasticity. If it can be rolled to the diameter of a pen and can support its own weight when draped over the side of the hand, the soil has high plasticity.

The Stick Test—The soil putty is rolled into a ball and stabbed with a knife. The amount of soil that clings to the knife when it is removed is observed. Soil sticking to the knife indicates clay content.

The Shine Test—The ball of soil putty is cut in half with a knife. The cross section of the ball is observed. A glossy/shine cross section indicates clay content, a dull cross section indicates higher silt or sand content.

Test Tube Particle Gradation—A dry sample is dispersed in water in a test tube marked "sand". The sample will start to slowly settle out of suspension at the bottom of the test tube. After different time increments, the portion of the sample remaining in suspension is transferred to a "silt" test tube and then to a "clay" test tube. Essentially, the test uses gravity to separate the soil sample into different groups based on particle size, and can give an approximation of the soil's particle gradation and fines content.

The Jar Test—The sample is dispersed in water inside of a jar. Once all of the sample settles out of suspension, different strata within the sample can be observed. These layers correspond to different particle sizes, although it is difficult to tell between finer sands and coarser silts and clays using this. This test has proven to be most valuable when used as a measure of the expansiveness of a soil. A soil that expands significantly after the introduction of water is likely to cause problems with shrinkage cracks if used to produce CEBs without enough stabilizer.

The names of the above tests differ by author, but the procedures are consistent for CEB and other earthen construction [1,8,10]. In order to use results from qualitative testing, each sample is assigned a score for each of the qualitative tests (i.e. the Pen, Stick, and Shine tests) based on that soil's performance in the test. The numbers from the quantitative tests (i.e. the Test Tube and Jar tests) are used directly.

The score assignments for the qualitative tests are as follows:

Pen Test
1: The sample can be rolled to approximately the diameter of a ball-point pen and does not break when draped over the side of the hand.
0: The sample holds together and can be rolled out; however, it breaks before it reaches approximately the diameter of a ball-point pen or it breaks when draped over the side of the hand.
−1: The sample does not hold together or cannot be rolled out without crumbling.

Stick Test
1: When the knife is pulled out of the sample, there is soil clinging to the blade.
0: When the knife is pulled out of the sample, there are streaks of soil residue on the blade.
−1: When the knife is pulled out of the sample, the blade is clean.

Shine Test
1: When the soil ball is cut in half, the cross-section appears glossy and reflects light.
0: When the soil ball is cut in half, the cross-section appears somewhat glossy but does not reflect light very well.
−1: When the soil ball is cut in half, the cross-section appears dull and does not reflect light.

Raw Inputs and Targets. In order to gather the data for the training dataset, 33 soil samples were provided by Dwell Earth, Inc. This provided the training inputs and targets necessary for network training as shown in Table 1.

TABLE 1

Raw inputs and targets for network training

| Sample No. | Inputs | | | | | Targets |
|---|---|---|---|---|---|---|
| | Pen | Stick | Shine | % Fines | % Expansion | Classification # |
| 1 | −1 | −1 | −1 | 0.00 | 0.00 | 2 |
| 2 | 0 | 0 | 0 | 75.00 | 21.37 | 9 |
| 3 | 0 | 0 | 0 | 87.50 | 22.50 | 11 |
| 4 | 1 | 1 | 1 | 62.50 | 60.00 | 12 |
| 5 | 1 | 1 | 1 | 62.50 | 32.60 | 1 |
| 6 | 1 | 1 | 1 | 95.00 | 0.00 | 6 |
| 7 | −1 | 0 | −1 | 37.50 | 21.00 | 3 |
| 8 | 1 | 0 | 0 | 62.50 | 7.69 | 4 |
| 9 | 1 | 1 | 1 | 68.75 | 46.15 | 8 |
| 10 | 1 | 1 | 1 | 93.75 | 45.45 | 5 |
| 11 | 1 | 1 | 1 | 75.00 | 50.00 | 5 |
| 12 | 1 | 1 | 1 | 62.50 | 43.33 | 5 |
| 13 | 1 | 1 | 1 | 62.50 | 9.52 | 6 |
| 14 | 0 | 0 | 1 | 56.25 | 14.00 | 4 |
| 15 | 1 | 1 | 1 | 43.75 | 33.33 | 10 |
| 16 | 0 | 0 | 0 | 50.00 | 12.90 | 4 |
| 17 | −1 | 0 | −1 | 40.00 | 25.00 | 11 |
| 18 | 0 | −1 | 0 | 50.00 | 0.00 | 3 |
| 19 | 1 | 1 | 1 | 62.50 | 5.13 | 6 |
| 20 | 0 | 0 | 0 | 37.50 | 0.00 | 3 |
| 21 | 0 | 0 | 0 | 31.25 | 30.77 | 3 |
| 22 | 1 | 0 | 0 | 56.25 | 59.46 | 6 |
| 23 | 0 | 0 | 0 | 75.00 | 50.00 | 6 |
| 24 | 1 | 0 | 1 | 62.50 | 25.58 | 5 |
| 25 | 1 | 0 | −1 | 37.50 | 4.55 | 5 |
| 26 | 1 | 0 | −1 | 70.00 | −2.13 | 6 |
| 27 | −1 | −1 | −1 | 60.00 | 9.17 | 3 |
| 28 | −1 | −1 | −1 | 60.00 | 20.80 | 3 |
| 29 | −1 | 0 | −1 | 91.25 | 18.52 | 3 |
| 30 | −1 | −1 | −1 | 37.50 | 11.11 | 3 |
| 31 | −1 | 1 | −1 | 25.00 | 17.54 | 7 |
| 32 | 1 | 0 | −1 | 62.50 | 36.36 | 7 |
| 33 | 1 | −1 | −1 | 62.50 | 2.33 | 6 |

TABLE 1

USCS classifications

| Network Classification | USCS Group Symbol | USCS Group Name |
|---|---|---|
| 1 | SW | Well-graded sand |
| 2 | SP | Poorly-graded sand |
| 3 | SM | Silty sand |
| 4 | SC-SM | Silty clayey sand |
| 5 | SC | Clayey sand |
| 6 | CL | Lean clay |
| 7 | ML | Sandy silt |
| 8 | CH | Fat clay |
| 9 | SW-SM | Well-graded sand with silt |
| 10 | SW-SC | Well-graded sand with clay |
| 11 | SP-SM | Poorly-graded sand with silt |
| 12 | SP-SC | Poorly-graded sand with clay |

Figure 3:
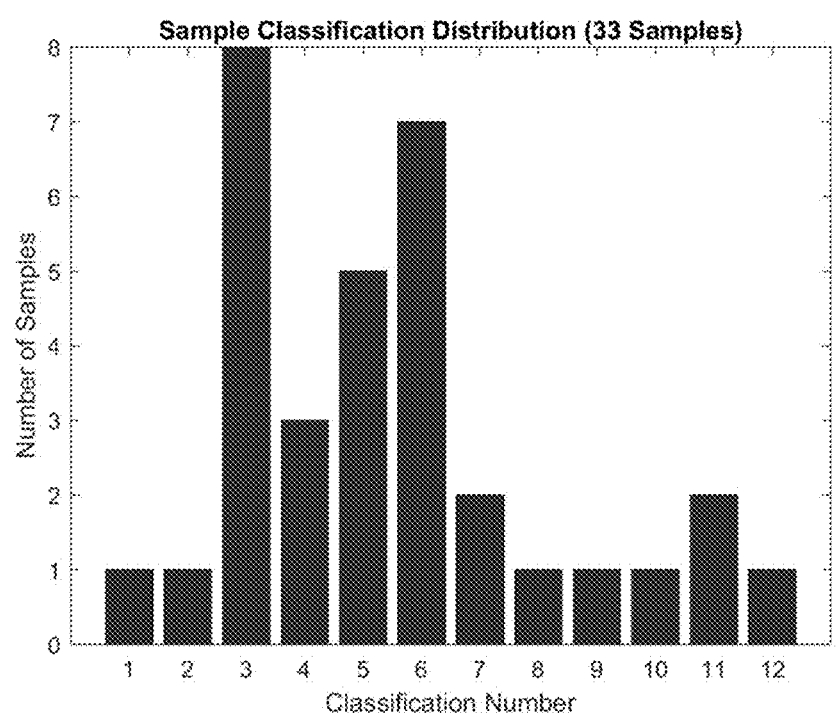
FIG. 3 is a graph that shows a raw sample classification distribution.
Figure 4:
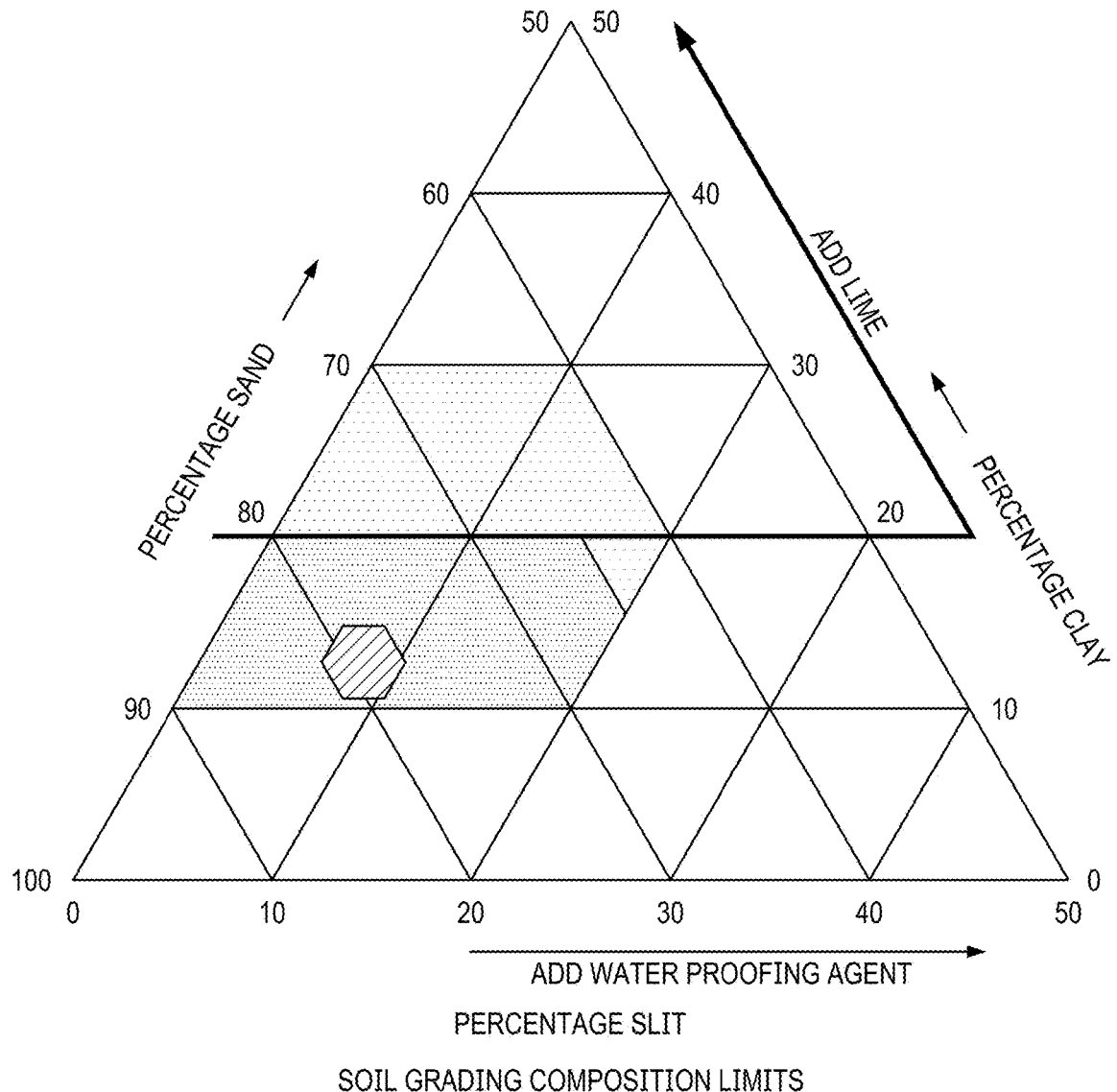
FIG. 4 shows a soil texture triangle with ideal soil types for CEB construction for use with, and implementation of, the present invention.

In this example, 12 unique USCS classifications were represented within the soils tested and are analysed in this paper, shown in Table 2, and the frequency of those classifications within the raw sample dataset is shown in FIG. 3. In addition, 23 possible classifications were considered, however not all classifications are suitable for CEB production. Immediately, soils that are predominantly gravel can be eliminated as candidate soils for CEB production, as can soils that are predominantly silt or clay (these can be used with the addition of an aggregate, but this would effectively change the soil classification). The 12 classifications present in the data sufficiently cover the most suitable soil types for CEB production. FIG. 4 shows visually the range of ideal soil types for CEB construction as given by CEB experts [30]. Most soils can be amended to fit within this group of soil types.

Figure 5:
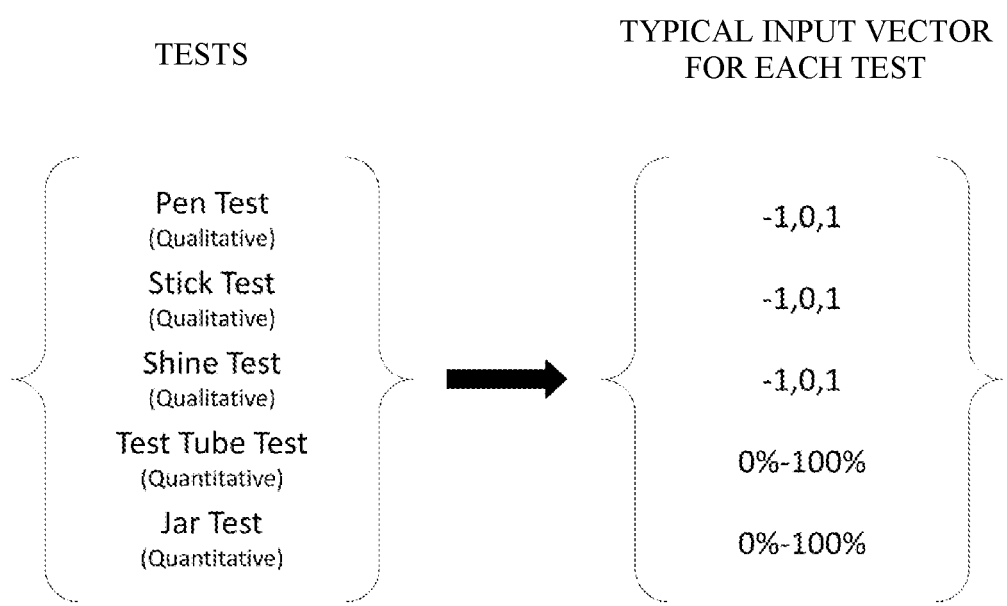
FIG. 5 shows a network input vector of the present invention.

FIG. 5 illustrates the ranges of a typical input vector for the neural network after data from the field soil analysis has been compiled using the present invention.

Training and Validation Data. To train the network and evaluate performance, two datasets were created from the collected soil data. While the coverage of soils that are appropriate for CEB construction is sufficient within the raw sample dataset, the quantity of samples is insufficient for proper training of a neural network. To account for this, as well as to account for inherent error involved in the soil testing process, noise was added to the raw dataset and additional, synthetic noisy data streams were created. Noise was added to the quantitative data as a percentage error. Noise was added to the scores from the qualitative tests by shifting scores by either 1 or −1; this shift represents an incorrect qualitative assignment by the individual executing the field test. The data points with noise added were stored as additional data points, thus expanding the dataset available for network training and validation. Synthetic data streams provide additional data streams with which to train robust, noise-tolerant neural classifiers. The quantitative noise was varied from 0% to 25% in increments of 5% for the two quantitative attributes of the input vectors. The noise is added directly to the results from the quantitative tests.

Qualitative tests are subjective in nature and may vary for different individuals testing the same soil. To increase the robustness of the network to include this subjective character, noise was added to qualitative test indications. Qualitative noise was represented by randomly designating the indicator (i.e. −1,0,1) for one, two, or all three quantitative field tests.

In total, 24 unique data sets were considered: the original experimental data set and 23 additional synthetic data sets created by adding quantitative and qualitative noise. For each percent error added to the quantitative noise (0%-25% in 5% increments), qualitative noise was added in the form of 0, 1, 2, or 3 incorrectly assigned qualitative assessments.

Figure 6:
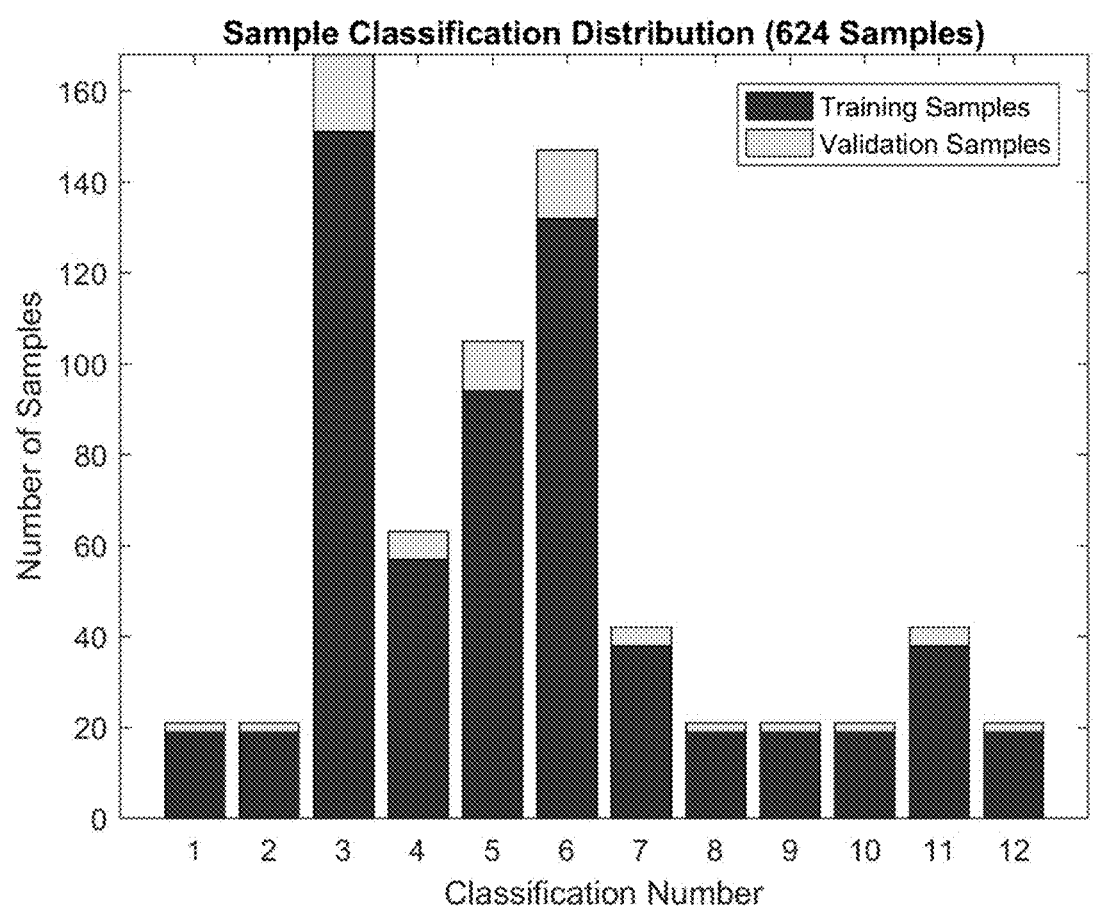
FIG. 6 is a graph that shows a noisy sample classification distribution.

To select training and validation data, individual input/output groups from all data sets (including noisy data streams) were organized by soil classification. 10% of the samples from each classification grouping were randomly selected and set aside for network validation after training, with the remainder of the input dataset being used as the training dataset for the network. FIG. 6 shows the noisy sample classification distribution for an input data set after noise has been added. The bars are divided to show the number of samples used for training and held for validation.

Figure 7:
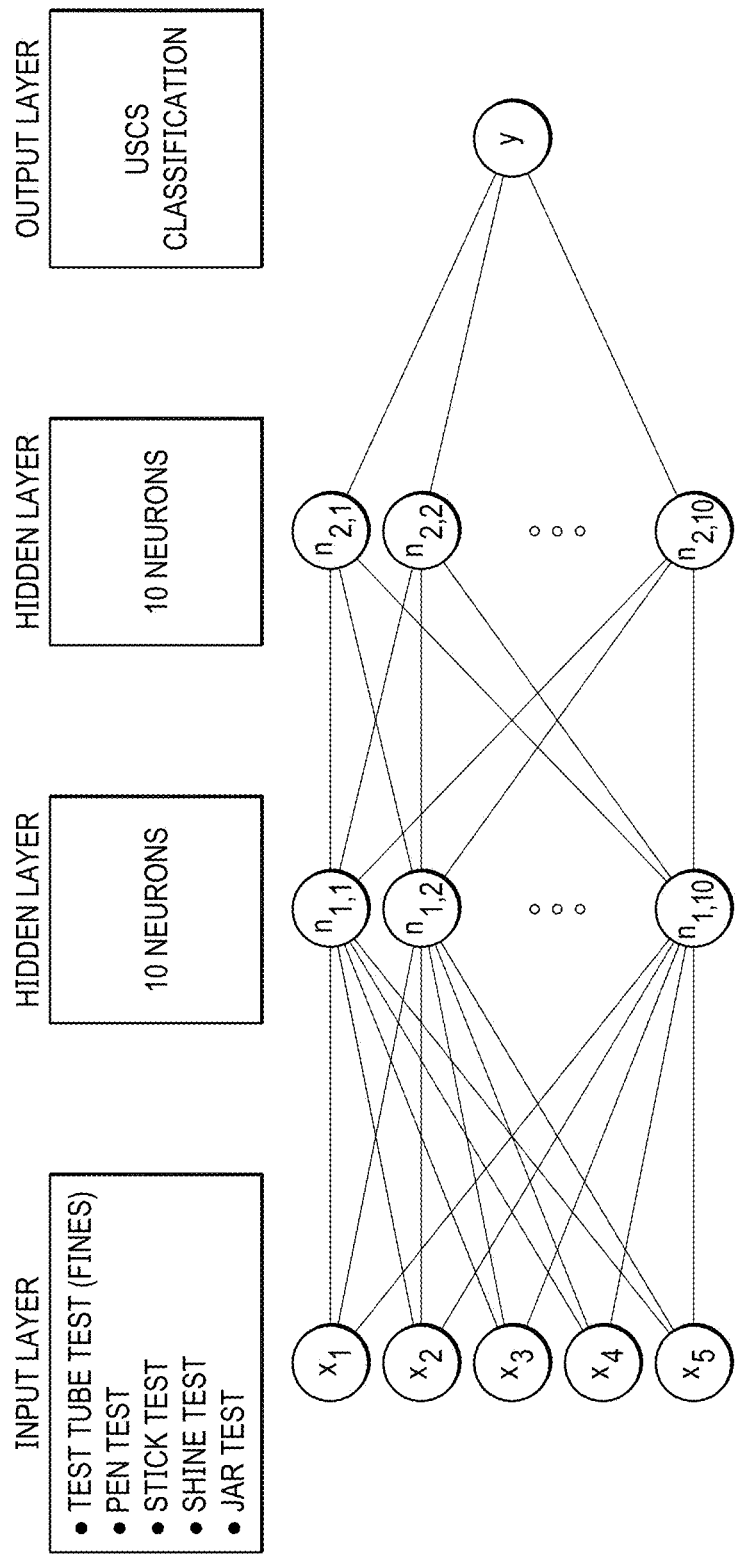
FIG. 7 is a diagram that shows a neural network architecture used with the present invention.

Neural Network Architecture. FIG. 7 shows a simple input-output model of the neural network structure used. All the networks used in this research contained two hidden layers with 10 neurons in each layer. A scaled conjugate gradient backpropagation training function was used. A logarithmic sigmoid transfer function was used in both hidden layers. FIG. 7 shows the architecture of the networks used.

Figure 8:
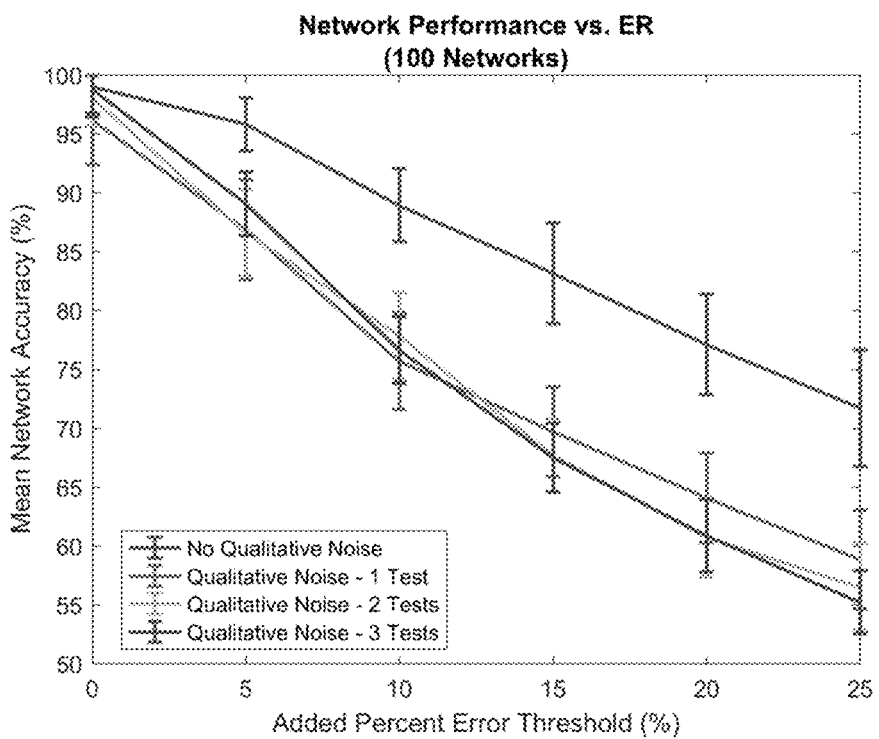
FIG. 8 is a graph that shows the mean network accuracy vs. added percent error threshold (quantitative).

Neural Network Performance. Full Datasets. As mentioned previously, 10% of each noisy input dataset was set aside for network validation and performance evaluation. In order to assess network performance, 100 networks were trained on each of the 24 training datasets representing a specific combination of quantitative and qualitative noise (2400 total networks). Each network was validated on the corresponding validation dataset and the soil classifications produced by the network were compared to the validation targets. FIG. 8 shows network performance for each of the 24 full datasets using the method of the present invention. Performance is given as the mean percent correct during validation for the 100 networks trained on each full data set and validated on that data set. The error bars show one standard deviation in the positive and negative direction.

It was found that mean network accuracy decreased with increasing levels of noise added to the quantitative data. It was also found that mean network accuracy decreased with the addition of qualitative noise. Interestingly, however, network performance did not fluctuate appreciably when noise was added to an increasing number of qualitative tests.

The validation results from a network trained using 10% quantitative noise and no qualitative noise are given in Table 3. Each column represents the correct classification for a validation sample. Each row represents the classification assigned to a validation sample by the networks. Green cells indicate a correct classification. For example, Table 3 shows that the networks correctly classified 64.0% of the samples that are classification 1, and incorrectly classified samples that are classification 1 as classifications 5, 6, 8, 10, and 12, in varying quantities.

data, the networks performed with 51.38% accuracy. After being trained on the dataset containing only quantitative data, the networks performed with 50.59% accuracy during validation.

Application. While a mean performance of 89.35% for a single network trained using a full dataset shows the capabilities of the neural networks to rapidly and accurately classify a soil, accuracy can be improved for field implementation by using a series of trained neural networks. The authors suggest that the output classification should be the mode of the classifications output by a sufficient number of trained networks; 100 were used to obtain the mean performance and standard deviation results in the previous section. This reduces the potential for a misclassification due to a single network making an incorrect prediction.

The reduction in performance resulting from the addition of qualitative noise to a single qualitative input is expected; however, this performance does not decrease appreciably with the introduction of noise to additional qualitative inputs. This behavior may result from the reduction of emphasis placed on qualitative data in the neural network. As the network is trained, weights are updated in such a manner so that patterns of incorrect qualitative data do not

TABLE 3

Output classification vs. target classification for network validation

| | | TARGET CLASS | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| OUTPUT CLASS | 1 | 64.0% | | | | 4.2% | 0.1% | | 5.0% | | 7.0% | | |
| | 2 | | 100.0% | 0.1% | | | | | | | | | |
| | 3 | | | 94.2% | 2.0% | | | | | | | 12.8% | |
| | 4 | | | 0.4% | 97.7% | | 0.1% | | 2.5% | | | | |
| | 5 | 29.0% | | | | 87.0% | 0.2% | 9.8% | 66.5% | | | | 19.5% |
| | 6 | 0.5% | | | 0.2% | 0.1% | 99.4% | 0.3% | | 1.0% | | | |
| | 7 | | | 0.1% | | 3.2% | | 90.0% | | | | | |
| | 8 | 0.5% | | | | 3.1% | | | 14.5% | | | | 9.5% |
| | 9 | | | 0.1% | 0.2% | | 0.1% | | 75.5% | | | 9.0% | |
| | 10 | 5.5% | | | | 0.5% | | | | | 93.0% | | |
| | 11 | | | 5.2% | | | 0.1% | | 21.0% | | | 78.3% | |
| | 12 | 0.5% | | | | 2.0% | | | 14.0% | | | | 71.0% |

Partial Datasets. To investigate the ability of the networks to fuse qualitative and quantitative data in order to make a prediction, sets of networks were trained on partial datasets. One set of networks was trained on only the qualitative test data, and another was trained on only the quantitative test data. 10% noise was added to the quantitative data. No noise was added to the qualitative data. Table 4 shows the mean performance and standard deviation for 100 networks trained on the full input dataset, only the qualitative test data, and only the quantitative test data.

TABLE 4

Network performance for full vs. partial datasets

| | Mean Performance | Standard Deviation |
|---|---|---|
| Full Dataset | 89.35% | 3.18% |
| Quantitative Only | 50.59% | 5.00% |
| Qualitative Only | 51.38% | 3.27% |

Network performance was severely impacted by training the networks on partial datasets. After being trained on a full data set, the networks performed with 89.35% accuracy. After being trained on the dataset containing only qualitative impact the results negatively. Effectively, the network can detect patterns that are likely flawed and deemphasizes those inputs. This feature reinforces the notion that neural classifiers can be trained to be robust in the presence of flawed data produced by human errors or malfunctioning sensors [20].

Table 3 shows that there are patterns in how the networks misclassify different types of soil, i.e. if the networks misclassify a soil type, there are typically one or two classifications it will misclassify the soil as. For example, if the networks misclassify a soil that is classification 1, Table 3 shows that the networks will typically misclassify the soil as classification 5, with the slight possibility of a different classification. This pattern is an indicator that while the networks are misclassifying a soil, they are doing so with consistency. FIG. 6 shows that some soil classifications are not as heavily represented as others in the training data set; most of the misclassifications are due to the networks classifying soils that belong to these classifications as classifications with which the networks are more familiar.

The performance decrease seen by training the networks on partial datasets instead of the full dataset indicates two primary findings. First, the networks are capable of combining qualitative and quantitative data streams to make more accurate predictions. Second, both the qualitative and quantitative data streams are important to the networks learning and making accurate predictions.

This discrepancy between the performances of the networks trained on the partial datasets and the performances of the networks trained on the full dataset indicates that the soil characteristics needed to effectively classify the soil for USCS are not solely contained in either the quantitative data or the qualitative data. In order to assign a soil a USCS classification, there are three basic properties of the soil that need to be known: percent gravel, percent fines (silt and clay), and the plasticity index (liquid limit and plastic limit). The qualitative data stream contains the results from the pen, stick, and shine tests, which give information about a soil's plasticity and the breakdown of the fines portion of a soil (i.e. clay content vs. silt content). The quantitative data stream contains the results from the test tube and jar tests, which give information about a soils particle distribution and how much a soil expands when it is saturated with water. If either qualitative or quantitative data stream is removed, the networks do not have the necessary information needed to adequately map the input-output space and model the USCS classification algorithm.

The present invention uses a framework in which qualitative and quantitative field data to obtain standardized soil classification. The framework is a neural evaluation system that compares input-output soil classification data and establishes a relationship between field data, laboratory data, and ultimately standardized soil classification. A series of neural networks were trained to assign soil classifications based on qualitative and quantitative field test data. It was found that the accuracy of the networks is dependent on the method and quantity of noise applied. Additionally, network performance decreases as inputs are removed from the system, meaning that both qualitative and quantitative data streams are important for network performance as each group contains vital diagnostic content.

The success of the networks described herein demonstrates that neural networks are able to make use of both qualitative and quantitative soil analysis data obtained in the field to provide a tight relationship between soil characteristics and CEB performance. Thus, the present invention uses neural networks to provide for the first time an efficient, robust solution for rapid soil classification for CEB construction in the field.

CEB Strength Testing

Figure 9:
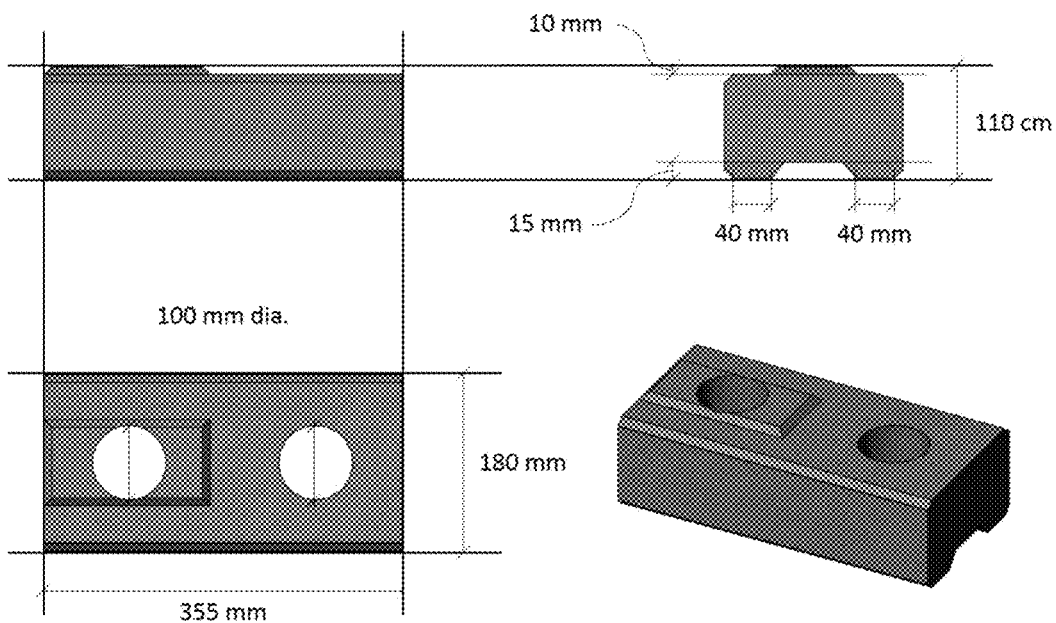
FIG. 9 is a 3-D computer model of a typical Ccompressed earth block (CEB) produced using the Earth Blox BP714.

Block Geometry and Production. Blocks for testing were produced using an Earth Blox BP714 machine. This machine uses a two-stage compression process to produce blocks with consistent size. Shape and dimensions for a CEB produced using the BP714 are shown via a 3-D computer model in FIG. 9. The geometry of these particular CEBs, with rails on the bottom surface and a tongue on the top surface, allows the blocks to be easily stacked while leaving a small gap between the middle sections of stacked bricks that can be filled with cement. These blocks are unique to CEB construction in that they contain holes, which allow for grouting and the installation of vertical reinforcement in wall construction to make a truly composite structural system.

These particular blocks were chosen due to the production consistency that can be obtained with the Earth Blox BP714. Many CEBs are produced using manual presses that rely on leverage to achieve proper compaction, however it is near impossible to be precise in the compactions pressures being used from brick to brick. A difference in compaction pressures can likely represent a significant difference in final block strengths; while this relationship is important, it fell outside of the intended scope of this particular project. Thus the BP714 was chosen in an effort to minimize the effect of differing compaction pressures on the results.

Mix Designs. Blocks were made using a total of 14 different mix designs. The mix design variables included soil to sand ratio (SSR), water content, and cement content. The soil type was held constant for all mix designs. Table 5 shows the specifications used for each mix design. Mixes 07, 08, 11, and 12 have "NO SAND" in the Soil/Sand Ratio column because no sand was added for those mixes. The SSR of each soil does not include the sand contained within the raw soil. The Soil Type column contains the Unified Soil Classification System (USCS) soil classification group label for the raw soil used, which was classified as silty-clayey sand. The stabilizer content for each mix is based on the dry volume of the mixture. The water content for each mix is based on the total volume of the mixture after water is added and includes the in-situ moisture from the raw soil.

Mixes were created by taking a known quantity of soil (27.5 gal) and calculating the appropriate quantities of additives needed to hit target marks for SSR, water content, and cement content. Sand and cement were added to the raw soil before the mixture was dumped into a bin mixer. The water was gradually added while the mixture was agitated by an auger. Once homogeneity was reached, the mixture was fed into the BP714 via a conveyor belt. The contents of Table 5 were calculated after the mixes were created using the actual quantities of additives used.

TABLE 5

Mix design specifications

| Mix Number | Soil Type | Soil/Sand Ratio | Stabilizer Type | Stabilizer Content | Water Content (%) |
|---|---|---|---|---|---|
| 01 | SC-SM | 3.73 | Portland Cement | 5.45% | 10.65% |
| 02 | SC-SM | 3.73 | Portland Cement | 9.09% | 10.44% |
| 03 | SC-SM | 3.55 | Portland Cement | 10.91% | 10.33% |
| 04 | SC-SM | 3.55 | Portland Cement | 5.45% | 11.72% |
| 05 | SC-SM | 3.36 | Portland Cement | 9.09% | 11.51% |
| 06 | SC-SM | 3.36 | Portland Cement | 10.91% | 11.40% |
| 07 | SC-SM | NO SAND | Portland Cement | 3.64% | 9.93% |
| 08 | SC-SM | NO SAND | Portland Cement | 3.64% | 8.39% |
| 09 | SC-SM | 2.53 | Portland Cement | 3.64% | 9.93% |
| 10 | SC-SM | 2.53 | Portland Cement | 3.64% | 8.39% |
| 11 | SC-SM | NO SAND | Portland Cement | 9.09% | 9.72% |
| 12 | SC-SM | NO SAND | Portland Cement | 9.09% | 8.18% |
| 13 | SC-SM | 2.33 | Portland Cement | 9.09% | 9.72% |
| 14 | SC-SM | 2.33 | Portland Cement | 9.09% | 8.18% |

Each mix design produced 11 blocks at minimum.

Table 6 shows how these 11 blocks were allocated for testing. Any blocks produced for a mix design beyond the planned 11 blocks were held as extra spare blocks.

TABLE 6

Block allocation for all mix designs

| Use | # Bricks |
|---|---|
| 3-Point Bending - 7D | 2 |
| 3-Point Bending - 28D | 2 |
| Direct Compression - 7D (Dry) | 2 |
| Direct Compression - 7D (Sat) | 1 |
| Direct Compression - 28D (Dry) | 2 |
| Direct Compression - 28D (Sat) | 1 |
| Spare | 1 |
| Total Bricks per Mix | 11 |

3-Point Bending Testing. 3-point bending testing uses a simply-supported beam configuration to test blocks in flexure. Two supports are placed under a block inset from either end, thus creating a simply-supported condition. A gradually increasing point load is distributed across the midspan of the block until failure occurs. Failure is expected to occur due to tension in the bottom face of the brick, not due to shear.

Figure 10A:
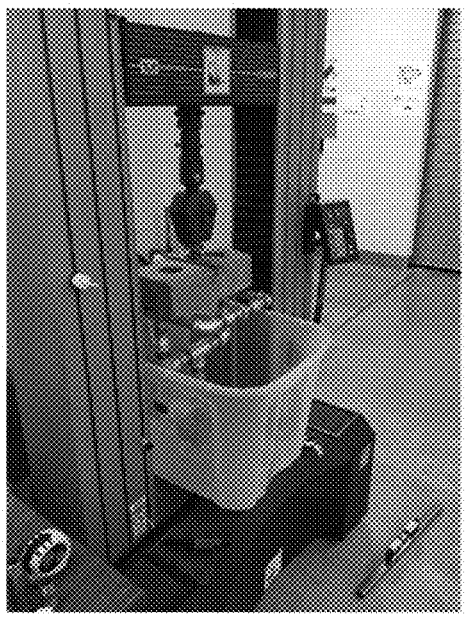
FIG. 10A and 10B show a 3-point bending test setup for testing the present invention.
Figure 10B:
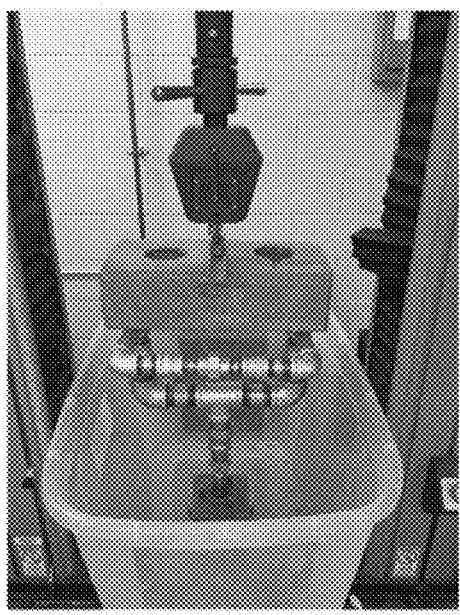
Figure 11A:
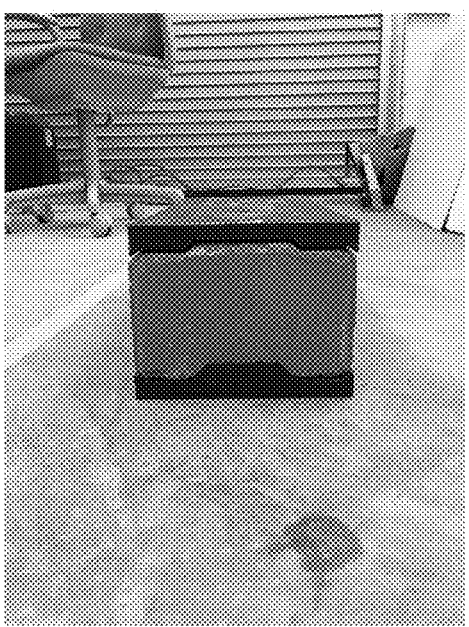
FIG. 11A and 11B show CEB with direct compression plates.
Figure 11B:

In order to perform 3-point bending testing, a support frame had to be constructed. The specifications outlined in ASTM C78 were followed as closely as possible (ASTM2016b). The frame was constructed using steel pipe and is shown in FIG. 10A and 10B. Load was applied using an Instron 5582 load frame and measured using an Instron 100 kN capacity load cell. The load was displacement-controlled and was increased at a rate of 0.013 mm/sec.

Load and displacement measurements were taken during testing until block failure occurred. In order to calculate the maximum tensile stress in the blocks at failure, the following equation was used:

$$\sigma = \frac{My}{I} \quad (3.1)$$

where:
σ=calculated bending stress at given location (psi)
M=internal bending moment about the neutral axis at given location (lb.*in.)
y=perpendicular distance from the neutral axis to the bottom fiber (in.)
I=second moment of area about the neutral axis (in.$^4$)

Direct Compression Testing. Perhaps the most valuable CEB strength information can be found through direct compression testing, whereby blocks are placed between steel plates that conform to their geometry and a gradually increasing load is applied perpendicular to the block's main surface (top) until failure occurs. The load is load-controlled and is increased at a rate of 172-344 kPa/sec. The plates on the top and bottom of the brick are rigid. Direct compression testing more closely resembles the types of loads the blocks are likely to experience in construction than 3-point bending testing does. FIGS. 10A and 10B show a block with the plates used for direct compression. The plates are taken directly from a mold used to produce the blocks, so they fit the block's unique geometry.

ASTM has published standards governing compression testing of SMU and other masonry prisms, however they do not explicitly address compressed (ASTM2017 and ASTM2016b). Section 14.7.4.23 of the New Mexico Earthen Building Materials Code mandates that blocks must be tested in a flat position using a true platen and a swivel head to account for nonparallel bearing surfaces (NMAC2009). These guidelines were followed as closely as possible during testing and are incorporated herein by reference.

Due to the capacity limitations of the Instron 5582 load frame that was used for 3-point bending testing, blocks were unable to be tested in direct compression in the SMU structures and materials laboratory. Instead, a local materials testing company, GME Consulting, was hired to perform the testing using their compression testing machine. SMU personnel were onsite to assist in the testing of the blocks and recording of the data.

Load measurements were taken during testing until block failure occurred. In order to calculate the maximum compressive stress in the blocks at failure, the following equation was used:

$$\sigma = \frac{P}{A} \quad (3.2)$$

where:
σ=calculated normal stress (psi)
P=measured applied load (lbs.)
A=area of the surface on which the load is applied (in.$^2$)

Some blocks were tested in a fully-saturated state, meaning they were submerged in a bucket of water at least 12 hours prior to testing. Due to the inherent permeability of the blocks, blocks were wet throughout their cross-sections at the time of testing.

Test Results. The results from the 7-day and 28-day 3-point bending testing are shown in Table 6 and 7, respectively.

TABLE 7

7-day 3-point bending test results

| Block Number | Mix Number | Stabilizer Content | Water Content | Soil to Sand Ratio (SSR) | Peak Load (kN) | Maximum Stress (kPa) |
|---|---|---|---|---|---|---|
| 3P01 | 01 | 5.45% | 10.65% | 3.73 | 2.65 | 730.87 |
| 3P02 | 01 | 5.45% | 10.65% | 3.73 | 2.83 | 780.51 |
| 3P03 | 02 | 9.09% | 10.44% | 3.73 | 3.52 | 970.82 |
| 3P04 | 02 | 9.09% | 10.44% | 3.73 | 3.71 | 1023.22 |
| 3P05 | 03 | 10.91% | 10.33% | 3.55 | 3.07 | 846.71 |
| 3P06 | 03 | 10.91% | 10.33% | 3.55 | 3.82 | 1053.56 |
| 3P07 | 04 | 5.45% | 11.72% | 3.55 | 4.96 | 1367.97 |
| 3P08 | 04 | 5.45% | 11.72% | 3.55 | 3.62 | 998.40 |
| 3P09 | 05 | 9.09% | 11.51% | 3.36 | 4.51 | 1243.86 |
| 3P10 | 05 | 9.09% | 11.51% | 3.36 | 4.41 | 1216.28 |
| 3P11 | 06 | 10.91% | 11.40% | 3.36 | 4.05 | 1116.99 |
| 3P12 | 06 | 10.91% | 11.40% | 3.36 | 4.61 | 1271.44 |
| 3P25 | 07 | 3.64% | 9.93% | NO SAND | 2.02 | 557.12 |
| 3P26 | 07 | 3.64% | 9.93% | NO SAND | 2.72 | 750.18 |
| 3P27 | 08 | 3.64% | 8.39% | NO SAND | 2.18 | 601.24 |
| 3P28 | 08 | 3.64% | 8.39% | NO SAND | 1.50 | 413.70 |
| 3P29 | 09 | 3.64% | 9.93% | 2.53 | 2.28 | 628.82 |
| 3P30 | 09 | 3.64% | 9.93% | 2.53 | 2.84 | 783.27 |
| 3P31 | 10 | 3.64% | 8.39% | 2.53 | 1.77 | 488.17 |
| 3P32 | 10 | 3.64% | 8.39% | 2.53 | 2.23 | 615.03 |
| 3P33 | 11 | 9.09% | 9.72% | NO SAND | 4.19 | 1155.60 |
| 3P34 | 11 | 9.09% | 9.72% | NO SAND | 3.08 | 849.46 |
| 3P35 | 12 | 9.09% | 8.18% | NO SAND | 1.86 | 512.99 |

TABLE 7-continued 7-day 3-point bending test results

| Block Number | Mix Number | Stabilizer Content | Water Content | Soil to Sand Ratio (SSR) | Peak Load (kN) | Maximum Stress (kPa) |
|---|---|---|---|---|---|---|
| 3P36 | 12 | 9.09% | 8.18% | NO SAND | 2.57 | 708.81 |
| 3P37 | 13 | 9.09% | 9.72% | 2.33 | 5.66 | 1561.03 |
| 3P38 | 13 | 9.09% | 9.72% | 2.33 | 4.30 | 1185.94 |
| 3P39 | 14 | 9.09% | 8.18% | 2.33 | 3.51 | 968.06 |
| 3P40 | 14 | 9.09% | 8.18% | 2.33 | 3.78 | 1042.52 |

TABLE 8

28-day 3-point bending test results

| Block Number | Mix Number | Stabilizer Content | Water Content | Soil to Sand Ratio (SSR) | Peak Load (kN) | Maximum Stress (kPa) |
|---|---|---|---|---|---|---|
| 3P13 | 01 | 5.45% | 10.65% | 3.73 | 2.92 | 805.34 |
| 3P14 | 01 | 5.45% | 10.65% | 3.73 | 3.66 | 1009.43 |
| 3P15 | 02 | 9.09% | 10.44% | 3.73 | 4.20 | 1158.36 |
| 3P16 | 02 | 9.09% | 10.44% | 3.73 | 4.10 | 1130.78 |
| 3P17 | 03 | 10.91% | 10.33% | 3.55 | 3.78 | 1042.52 |
| 3P18 | 03 | 10.91% | 10.33% | 3.55 | 4.76 | 1312.81 |
| 3P19 | 04 | 5.45% | 11.72% | 3.55 | 5.14 | 1417.61 |
| 3P20 | 04 | 5.45% | 11.72% | 3.55 | 6.39 | 1762.36 |
| 3P21 | 05 | 9.09% | 11.51% | 3.36 | 5.26 | 1450.71 |
| 3P22 | 05 | 9.09% | 11.51% | 3.36 | 6.18 | 1704.44 |
| 3P23 | 06 | 10.91% | 11.40% | 3.36 | 6.01 | 1657.56 |
| 3P24 | 06 | 10.91% | 11.40% | 3.36 | 7.30 | 2013.34 |
| 3P41 | 07 | 3.64% | 9.93% | NO SAND | 2.06 | 568.15 |
| 3P42 | 07 | 3.64% | 9.93% | NO SAND | 3.13 | 863.25 |
| 3P43 | 08 | 3.64% | 8.39% | NO SAND | 0.60 | 164.65 |
| 3P44 | 08 | 3.64% | 8.39% | NO SAND | 0.82 | 225.33 |
| 3P45 | 09 | 3.64% | 9.93% | 2.53 | 3.35 | 923.93 |
| 3P46 | 09 | 3.64% | 9.93% | 2.53 | 3.31 | 912.90 |
| 3P47 | 10 | 3.64% | 8.39% | 2.53 | 2.23 | 615.03 |
| 3P48 | 10 | 3.64% | 8.39% | 2.53 | 2.90 | 799.82 |
| 3P49 | 11 | 9.09% | 9.72% | NO SAND | 2.32 | 639.86 |
| 3P50 | 11 | 9.09% | 9.72% | NO SAND | 4.51 | 1243.86 |
| 3P51 | 12 | 9.09% | 8.18% | NO SAND | 1.74 | 479.89 |
| 3P52 | 12 | 9.09% | 8.18% | NO SAND | 3.24 | 893.59 |
| 3P53 | 13 | 9.09% | 9.72% | 2.33 | 5.41 | 1492.08 |
| 3P54 | 13 | 9.09% | 9.72% | 2.33 | 5.87 | 1618.95 |
| 3P55 | 14 | 9.09% | 8.18% | 2.33 | 3.73 | 1028.73 |
| 3P56 | 14 | 9.09% | 8.18% | 2.33 | 4.70 | 1296.26 |

Figure 12:
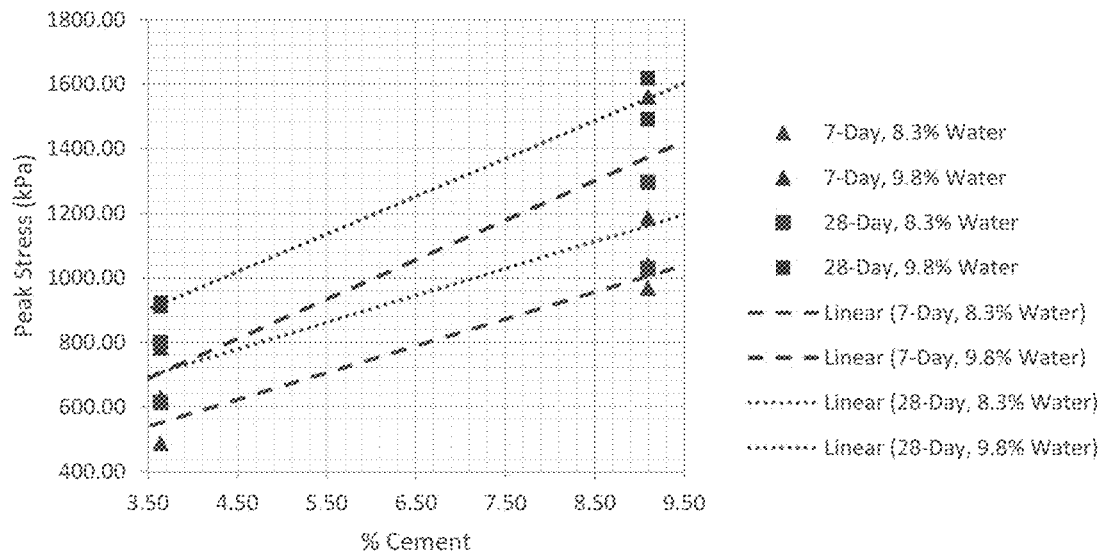
FIG. 12 shows two trends in the 3-point bending test results: the wetter mix was consistently stronger than the drier mix, and block strength increases with cement content.

FIG. 12 shows a plot of results from 3-point bending testing on blocks with an SSR of 2.4. The cement content of each block is shown on the x-axis, while the stress at which each block failed is shown on the y-axis. The colors indicate two different mixes, one drier mix and one wetter mix, and the shapes denote 7-day or 28-day bricks. Additional plots for mixes with different SSRs are given in FIGS. 14 to 21.

Test results for direct compression for 7-day and 28-day saturated blocks are shown in Table 9 and Table 10, respectively. Test results for direct compression for 7-day and 28-day dry blocks are shown in Table 11 and 12, respectively.

TABLE 9

7-day direct compression test results, saturated blocks

| Block Number | Mix Number | Stabilizer Content | Water Content | Soil to Sand Ratio (SSR) | Peak Load (kN) | Maximum Stress (kPa) |
|---|---|---|---|---|---|---|
| DCS01 | 01 | 5.45% | 10.65% | 3.73 | 174.05 | 3211.83 |
| DCS02 | 02 | 9.09% | 10.44% | 3.73 | 275.60 | 5085.74 |
| DCS03 | 03 | 10.91% | 10.33% | 3.55 | 321.55 | 5933.63 |
| DCS04 | 04 | 5.45% | 11.72% | 3.55 | 333.38 | 6151.97 |
| DCS05 | 05 | 9.09% | 11.51% | 3.36 | 355.84 | 6566.48 |
| DCS06 | 06 | 10.91% | 11.40% | 3.36 | 423.00 | 7805.90 |
| DCS07 | 07 | 3.64% | 9.93% | NO SAND | 189.35 | 3494.19 |
| DCS08 | 08 | 3.64% | 8.39% | NO SAND | 113.02 | 2085.68 |
| DCS09 | 09 | 3.64% | 9.93% | 2.53 | 209.81 | 3871.76 |
| DCS10 | 10 | 3.64% | 8.39% | 2.53 | 141.09 | 2603.61 |
| DCS11 | 11 | 9.09% | 9.72% | NO SAND | 261.01 | 4816.51 |
| DCS12 | 12 | 9.09% | 8.18% | NO SAND | 196.56 | 3627.16 |
| DCS13 | 13 | 9.09% | 9.72% | 2.33 | 428.97 | 7915.89 |
| DCS14 | 14 | 9.09% | 8.18% | 2.33 | 303.18 | 5594.64 |

TABLE 10

28-day direct compression test results, saturated blocks

| Block Number | Mix Number | Stabilizer Content | Water Content | Soil to Sand Ratio (SSR) | Peak Load (kN) | Maximum Stress (kPa) |
|---|---|---|---|---|---|---|
| DCS15 | 01 | 5.45 | 10.65 | 3.73 | 289.79 | 5347.57 |
| DCS16 | 02 | 9.09 | 10.44 | 3.73 | 396.81 | 7322.44 |
| DCS17 | 03 | 10.91 | 10.33 | 3.55 | 365.27 | 6740.49 |
| DCS18 | 04 | 5.45 | 11.72 | 3.55 | 315.32 | 5818.72 |
| DCS19 | 05 | 9.09 | 11.51 | 3.36 | 374.25 | 6906.29 |
| DCS20 | 06 | 10.91 | 11.40 | 3.36 | 445.29 | 8217.12 |
| DCS21 | 07 | 3.64 | 9.93 | NO SAND | 133.17 | 2457.50 |
| DCS22 | 08 | 3.64 | 8.39 | NO SAND | 172.49 | 3183.10 |
| DCS23 | 09 | 3.64 | 9.93 | 2.53 | 252.16 | 4653.17 |
| DCS24 | 10 | 3.64 | 8.39 | 2.53 | 199.05 | 3673.12 |
| DCS25 | 11 | 9.09 | 9.72 | NO SAND | 409.22 | 7551.45 |
| DCS26 | 12 | 9.09 | 8.18 | NO SAND | 216.66 | 3998.16 |
| DCS27 | 13 | 9.09 | 9.72 | 2.33 | 590.25 | 10892.14 |
| DCS28 | 14 | 9.09 | 8.18 | 2.33 | 265.46 | 4898.59 |

TABLE 11

7-day direct compression test results, dry blocks

| Block Number | Mix Number | Stabilizer Content | Water Content | Soil to Sand Ratio (SSR) | Peak Load (kN) | Maximum Stress (kPa) |
|---|---|---|---|---|---|---|
| DC01 | 01 | 5.45% | 10.65% | 3.73 | 261.05 | 4817.33 |
| DC02 | 01 | 5.45% | 10.65% | 3.73 | 434.17 | 8011.92 |
| DC03 | 02 | 9.09% | 10.44% | 3.73 | 444.76 | 8207.27 |
| DC04 | 02 | 9.09% | 10.44% | 3.73 | 591.72 | 10919.23 |
| DC05 | 03 | 10.91% | 10.33% | 3.55 | 422.07 | 7788.66 |
| DC06 | 03 | 10.91% | 10.33% | 3.55 | 552.98 | 10204.30 |
| DC07 | 04 | 5.45% | 11.72% | 3.55 | 651.50 | 12022.40 |
| DC08 | 04 | 5.45% | 11.72% | 3.55 | 666.49 | 12299.01 |
| DC09 | 05 | 9.09% | 11.51% | 3.36 | 801.53 | 14790.99 |
| DC10 | 05 | 9.09% | 11.51% | 3.36 | 677.70 | 12505.85 |
| DC11 | 06 | 10.91% | 11.40% | 3.36 | 648.34 | 11964.12 |
| DC12 | 06 | 10.91% | 11.40% | 3.36 | 804.20 | 14840.24 |

TABLE 11-continued 7-day direct compression test results, dry blocks

| Block Number | Mix Number | Stabilizer Content | Water Content | Soil to Sand Ratio (SSR) | Peak Load (kN) | Maximum Stress (kPa) |
|---|---|---|---|---|---|---|
| DC13 | 07 | 3.64% | 9.93% | NO SAND | 339.07 | 6257.03 |
| DC14 | 07 | 3.64% | 9.93% | NO SAND | 305.36 | 5634.86 |
| DC15 | 08 | 3.64% | 8.39% | NO SAND | 201.72 | 3722.37 |
| DC16 | 08 | 3.64% | 8.39% | NO SAND | 271.24 | 5005.30 |
| DC17 | 09 | 3.64% | 9.93% | 2.53 | 347.30 | 6408.88 |
| DC18 | 09 | 3.64% | 9.93% | 2.53 | 359.71 | 6637.89 |
| DC19 | 10 | 3.64% | 8.39% | 2.53 | 232.27 | 4286.27 |
| DC20 | 10 | 3.64% | 8.39% | 2.53 | 259.94 | 4796.81 |
| DC21 | 11 | 9.09% | 9.72% | NO SAND | 449.11 | 8287.71 |
| DC22 | 11 | 9.09% | 9.72% | NO SAND | 468.91 | 8652.97 |
| DC23 | 12 | 9.09% | 8.18% | NO SAND | 287.61 | 5307.35 |
| DC24 | 12 | 9.09% | 8.18% | NO SAND | 350.59 | 6469.62 |
| DC25 | 13 | 9.09% | 9.72% | 2.33 | 600.30 | 11077.65 |
| DC26 | 13 | 9.09% | 9.72% | 2.33 | 677.47 | 12501.75 |
| DC27 | 14 | 9.09% | 8.18% | 2.33 | 442.26 | 8161.31 |
| DC28 | 14 | 9.09% | 8.18% | 2.33 | 525.53 | 9697.86 |

TABLE 12

28-day direct compression test results, dry blocks

| Block Number | Mix Number | Stabilizer Content | Water Content | Soil to Sand Ratio (SSR) | Peak Load (kN) | Maximum Stress (kPa) |
|---|---|---|---|---|---|---|
| DC29 | 01 | 5.45 | 10.65 | 3.73 | 416.87 | 7692.63 |
| DC30 | 01 | 5.45 | 10.65 | 3.73 | 456.59 | 8425.61 |
| DC31 | 02 | 9.09 | 10.44 | 3.73 | 654.21 | 12072.47 |
| DC32 | 02 | 9.09 | 10.44 | 3.73 | 649.81 | 11991.21 |
| DC33 | 03 | 10.91 | 10.33 | 3.55 | 659.50 | 12170.14 |
| DC34 | 03 | 10.91 | 10.33 | 3.55 | 617.25 | 11390.37 |
| DC35 | 04 | 5.45 | 11.72 | 3.55 | 702.70 | 12967.15 |
| DC36 | 04 | 5.45 | 11.72 | 3.55 | 619.21 | 11426.49 |
| DC37 | 05 | 9.09 | 11.51 | 3.36 | 688.19 | 12699.56 |
| DC38 | 05 | 9.09 | 11.51 | 3.36 | 735.30 | 13568.80 |
| DC39 | 06 | 10.91 | 11.40 | 3.36 | 789.88 | 14575.94 |
| DC40 | 06 | 10.91 | 11.40 | 3.36 | 851.88 | 15720.14 |
| DC41 | 07 | 3.64 | 9.93 | NO SAND | 406.19 | 7495.63 |
| DC42 | 07 | 3.64 | 9.93 | NO SAND | 418.69 | 7726.28 |
| DC43 | 08 | 3.64 | 8.39 | NO SAND | 266.12 | 4910.90 |
| DC44 | 08 | 3.64 | 8.39 | NO SAND | 286.54 | 5287.65 |
| DC45 | 09 | 3.64 | 9.93 | 2.53 | 400.14 | 7384.00 |
| DC46 | 09 | 3.64 | 9.93 | 2.53 | 381.06 | 7031.88 |
| DC47 | 10 | 3.64 | 8.39 | 2.53 | 350.86 | 6474.55 |
| DC48 | 10 | 3.64 | 8.39 | 2.53 | 355.62 | 6562.37 |
| DC49 | 11 | 9.09 | 9.72 | NO SAND | 648.30 | 11963.30 |
| DC50 | 11 | 9.09 | 9.72 | NO SAND | 615.47 | 11357.54 |
| DC51 | 12 | 9.09 | 8.18 | NO SAND | 503.11 | 9284.18 |
| DC52 | 12 | 9.09 | 8.18 | NO SAND | 495.28 | 9139.71 |
| DC53 | 13 | 9.09 | 9.72 | 2.33 | 825.68 | 15236.69 |
| DC54 | 13 | 9.09 | 9.72 | 2.33 | 723.20 | 13345.54 |
| DC55 | 14 | 9.09 | 8.18 | 2.33 | 625.52 | 11543.04 |
| DC56 | 14 | 9.09 | 8.18 | 2.33 | 503.65 | 9294.03 |

Figure 13:
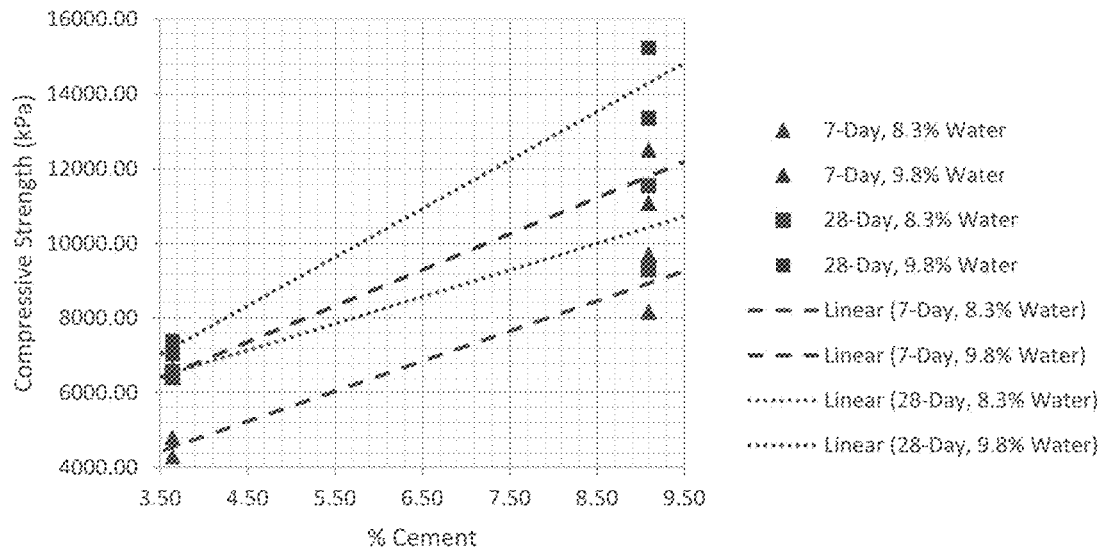
FIG. 13 shows a plot of results from direct compression testing on blocks with a soil to sand ratio (SSR) of 2.4.

FIG. 13 shows a plot of results from direct compression testing on blocks with an SSR of 2.4. The cement content of each block is shown on the x-axis, while the stress at which each block failed is shown on the y-axis. The colors indicate two different mixes, one drier mix and one wetter mix, and the shapes denote 7-day or 28-day bricks. Additional plots for mixes with different SSRs are shown in FIGS. 14 to 21.

FIG. 12 shows two trends in the 3-point bending test results: the wetter mix was consistently stronger than the drier mix, and block strength increases with cement content. These trends are present in the rest of the 3-point bending test results plots in FIGS. 14 to 21. The same trends shown in the results from 3-point bending testing can be seen in FIG. 13 as well as the rest of the direct compression data shown in FIGS. 14 to 21.

Figure 14:
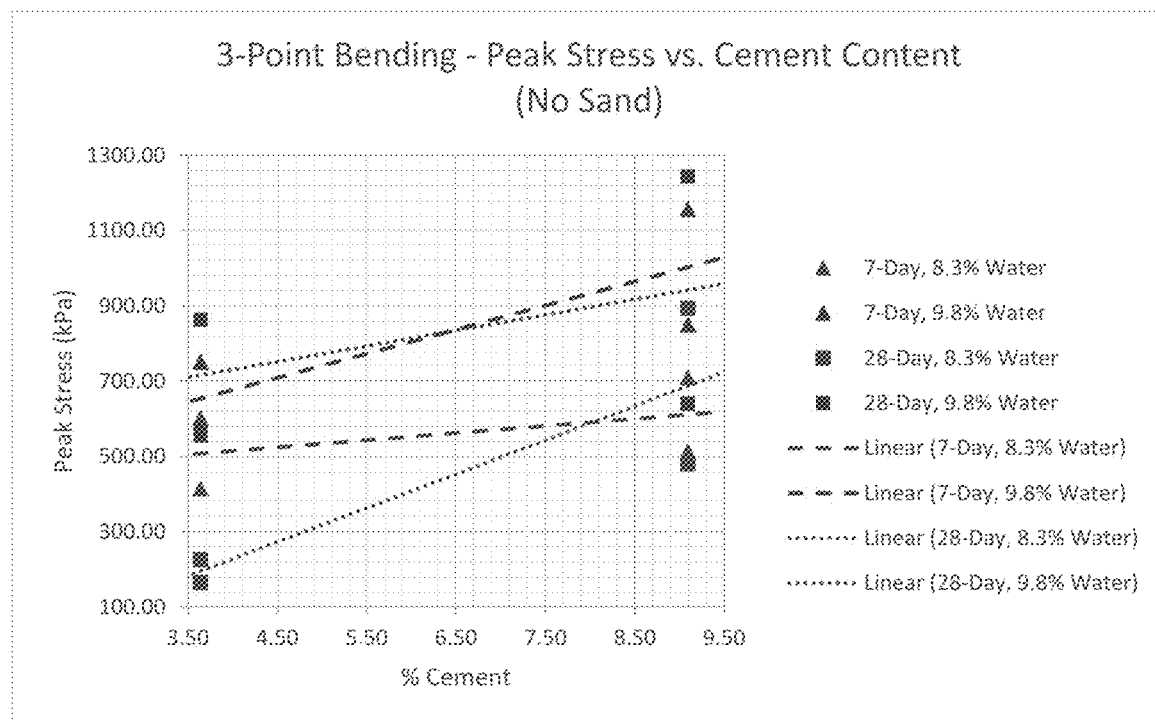
FIG. 14 shows a plot of 3-point bending-peak stress v. cement content (no sand).
Figure 15:
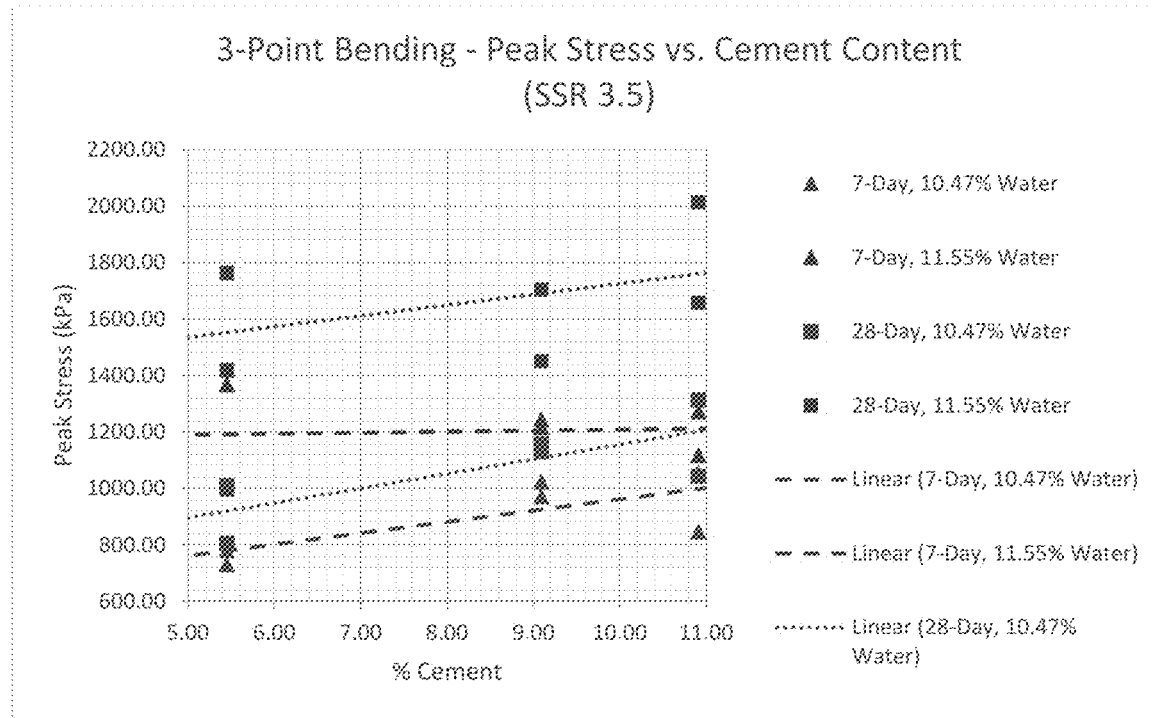
FIG. 15 shows a plot of 3-point bending-peak stress v. cement content (SSR 3.5).
Figure 16:
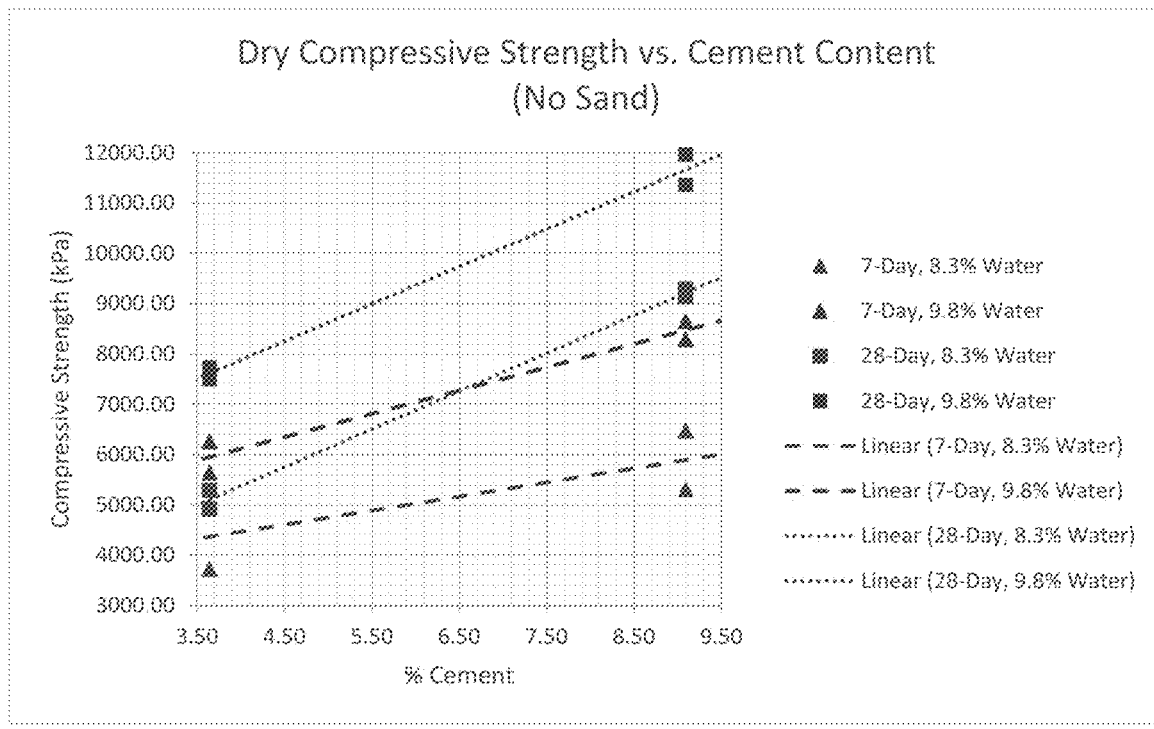
FIG. 16 shows a plot of dry compressive strength v. cement content (no sand).
Figure 17:
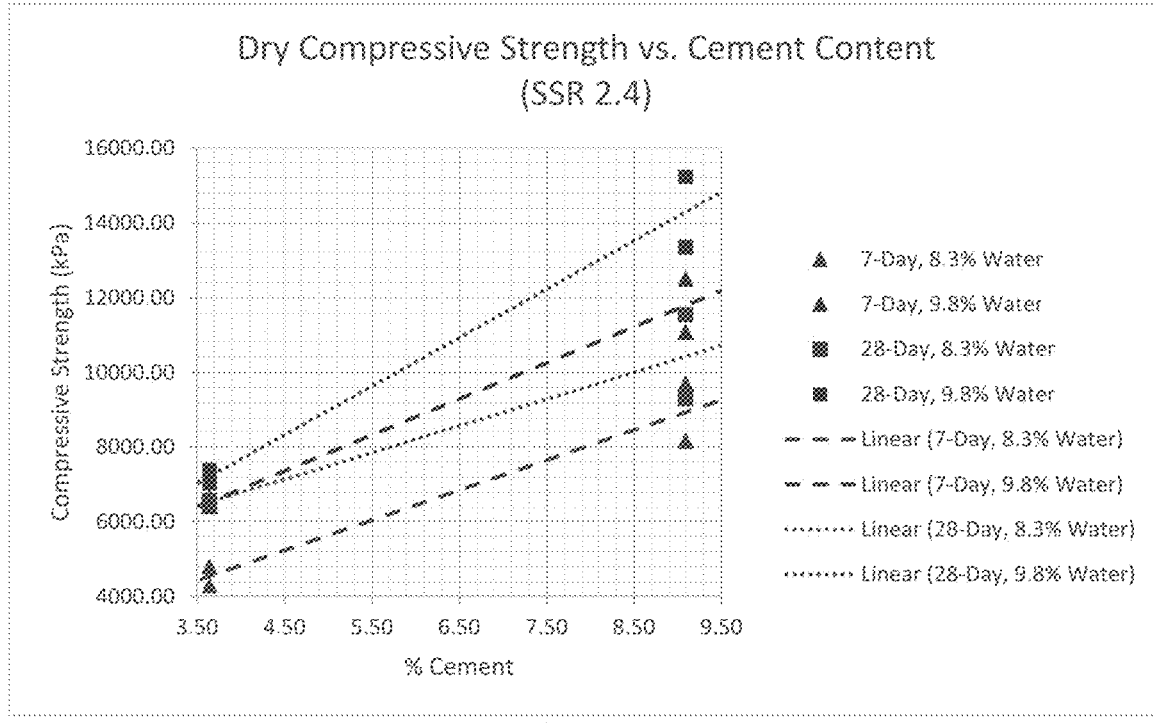
FIG. 17 shows a plot of dry compressive strength v. cement content (SSR 2.4).
Figure 18:
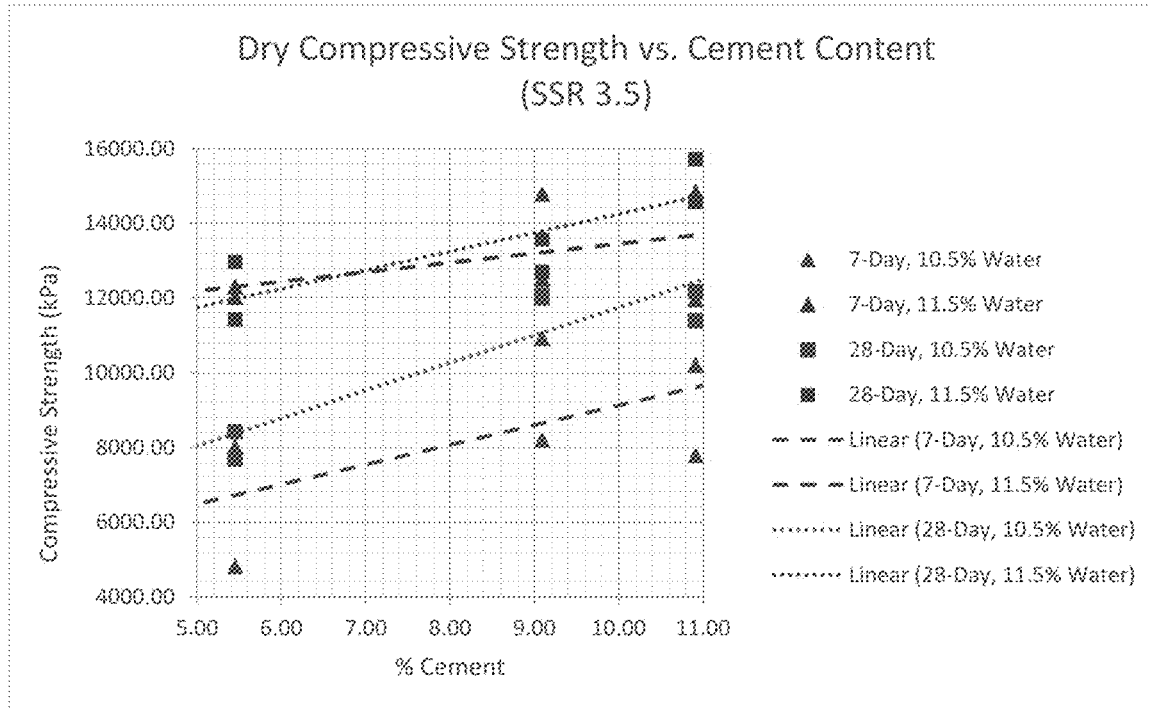
FIG. 18 shows a plot of dry compressive strength v. cement content (SSR 3.5).
Figure 19:
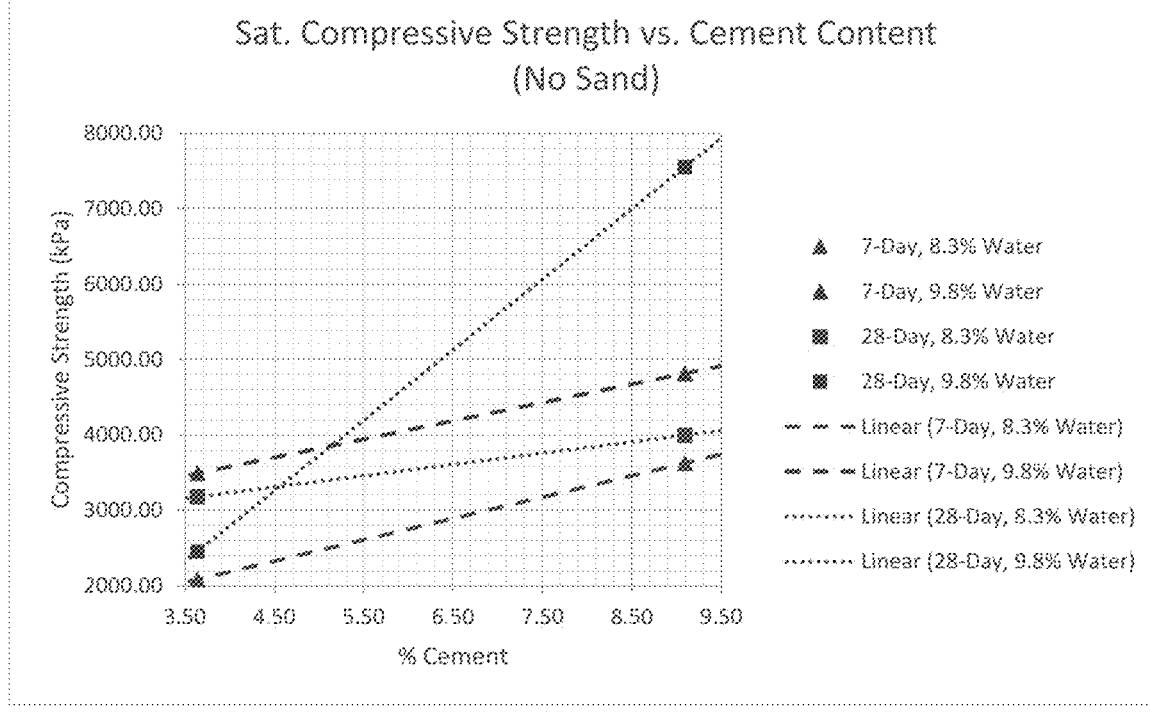
FIG. 19 shows a plot of a saturated compressive strength v. cement content (no sand).
Figure 20:
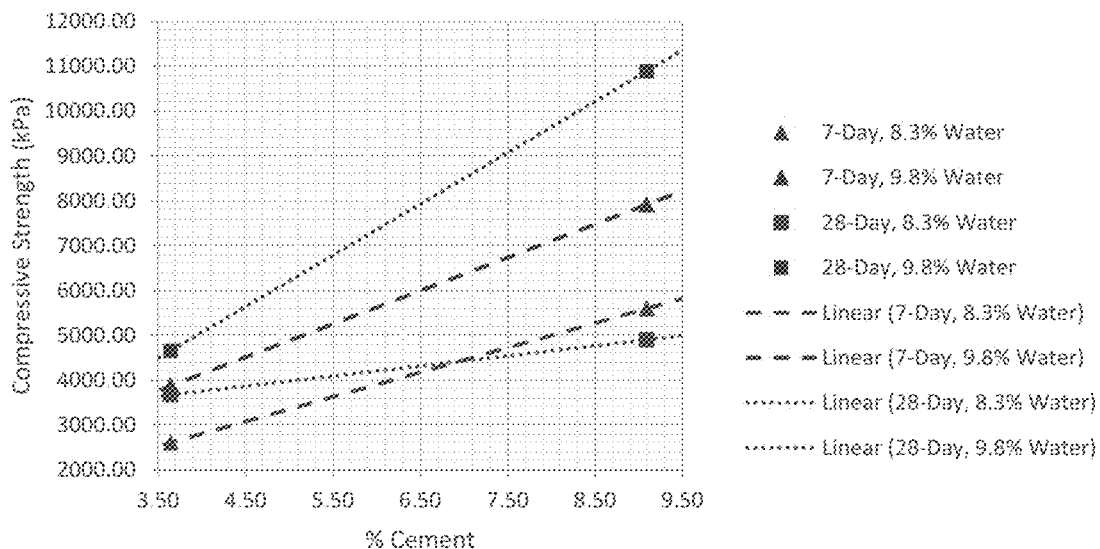
FIG. 20 shows a plot of a saturated compressive strength v. cement content (SSR 2.4).
Figure 21:
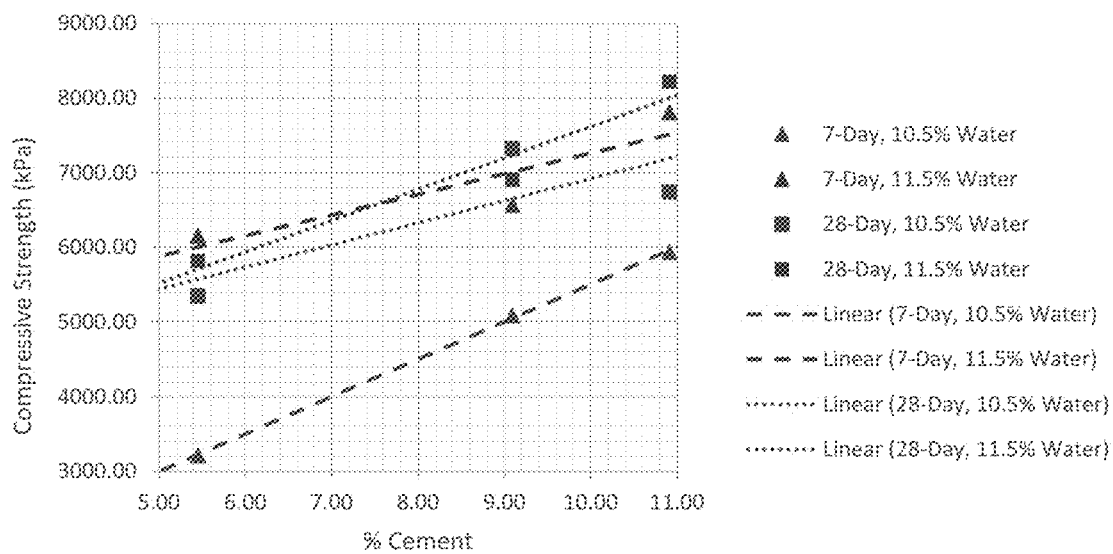
FIG. 21 shows a plot of a saturated compressive strength v. cement content (SSR 3.5).

FIG. 14 shows a plot of 3-point bending-peak stress v. cement content (no sand). FIG. 15 shows a plot of 3-point bending-peak stress v. cement content (SSR 3.5). FIG. 16 shows a plot of dry compressive strength v. cement content (no sand). FIG. 17 shows a plot of dry compressive strength v. cement content (SSR 2.4). FIG. 18 shows a plot of dry compressive strength v. cement content (SSR 3.5). FIG. 19 shows a plot of a saturated compressive strength v. cement content (no sand). FIG. 20 shows a plot of a saturated compressive strength v. cement content (SSR 2.4). FIG. 21 shows a plot of a saturated compressive strength v. cement content (SSR 3.5).

While the range of mix designs that was tested is limited, it can be reasonably concluded that there exists some optimal moisture content for each mix design and that none of the moisture contents used surpassed this optimal moisture content. The need for mixture in the mix design is twofold: the Portland cement used as stabilizer requires some amount of water to activate, and the clay present in the soil requires moisture to reach its plastic state, or the state in which it binds together and becomes moldable. If there is not sufficient moisture for both of these processes to occur, the final block will not be as strong.

The increase in strength seen with increasing amounts of stabilizer is relatively straightforward. Portland cement is better at binding the soil particles together than clay is on its own. However, as discussed hereinabove, the production of cement produces harmful greenhouse gases, so the environmental benefits of CEB are diminished as the cement content is increased.

It can be seen in Table 12 that the strongest 28-day blocks exceeded a compressive strength of 13,790 kPa (2000 psi). ASTM C90, which contains specifications for loadbearing concrete masonry units, mandates a minimum average compressive strength of 2000 psi (ASTM 2016c). This means that, with an optimal mix design, CEBs can be comparable in strength to CMU, which contain much more cement than CEB.

Block strength is the ultimate measure of performance for a CEB, as it governs how the CEB will perform under typical loading. A pilot run of blocks was created using 14 unique mix designs. Blocks from each mix design were tested in both 3-point bending as well as direct compression to study the effect of varying different mix design components on final block strength. Two predominant trends were observed: wetter mixes were consistently stronger than their dryer counterparts, and block strength increases with cement content. These trends can be seen in FIG. 13.

Additionally, the strongest mixes outperformed the ASTM minimum strength requirements for CMU, solidifying the notion that CEB should be considered a legitimate alternative to traditional masonry elements.

The primary contributions of this research are as follows: Rapid soil classification using artificial neural networks. A unique tool capable of rapidly and accurately assigning USCS soil classifications based on results from field soil analysis has been developed. The neural networks successfully fuse qualitative and quantitative data streams in order to make an accurate prediction.

Strength testing. ASTM standardized procedures designed for CMU and concrete are applied to a new CEB geometry. A pilot run of bricks was produced using one soil type to create 14 unique mix designs by varying water, stabilizer, and sand contents. The effect of varying mix design components on final block strength is studied, and two predominant trends are highlighted: Wetter mixes are consistently stronger than drier mixes with the same soil-to-sand ratio (SSR). Block strength increases as cement content is increased. Both rapid soil classification and strength testing are necessary to understand CEB performance and how it can be affected by soil type and mix design, especially once blocks are made using different soil types.

One example of a code for conducting the neural network analysis and soil classification is as follows, prepared in MatLab 2016b.

```
close all
clear all
clc
% save figures? (1 = yes, 0 = no)
printval = 1;
% variables
start = 2;
last_sample = 34;
inputNum = last_sample - 1;
quizPercent = 10; % number of samples to be held out of training for quizzing
possibleClasses = 12; % number of possible classifications
classes = 1:possibleClasses;
% saveRNG = rng;
% SNRvals = [5 10 15 20 25 30 35 40];
% SNRvals = 20;
% ERvals = 0:5:25;
ERvals = 10;
ERplotval = 10;
% noisyQual = [2 3];
% qualnum = 0:3;
qualnum = 0;
SNRplotval = 20;
NANDvals = 20;
crossEval = 1; % number of times to cross-evaluate
percentCorrect = zeros(crossEval,1);
storedQuizTarget = [ ];
storedQuizOutput = [ ];
for QUAL = 1:length(qualnum)
for k = 1:length(ERvals)
% load noisy data (from Yasha)
% strSNR = sprintf('SCDSwithNAND%iandSNR%i',NANDvals,SNRvals(k));
% load(strSNR)
% load('SCDSwithNAND20andQUAL2')
% strQUAL = num2str(qualnum(QUAL));
% strQUAL = strrep(strQUAL,' ',''');
% if isempty(noisyQual)~=1
% strQUAL = str2double(strQUAL);
% end
strER = sprintf('SCDSwithNAND%iandER%iandQUALNUM%i',NANDvals,ERvals(k),qualnum(QUAL));
load(strER)
totalNum = length(target);
rawTarget = target(:,1:inputNum);
loadedInput = input;
loadedTarget = target;
%*****************************
% % For quant only: (4:5,:)
% % For qual only: (1:3,:)
% input = input(1:3,:);
%sort the inputs and targets by classification
[target, targetIndex] - sort(target,'descend');
input = input(:,targetIndex);
%[target(4:5,1:33)' target(4:5,33:64)']
% initialize variables
sampleCounter = zeros(possibleClasses,1);
trainCounter = zeros(possibleClasses,crossEval);
quizCounter = trainCounter;
correct = zeros(possibleClasses,crossEval);
```

```
incorrect = correct;
% loop for cross-validation
counter = 0;
for z = 1:crossEval
    quizSamples = [ ];
    % sample evenly from each classification
    sampQuizNum = zeros(possibleClasses,1);
    sampleQuizPercent = zeros(possibleClasses,1);
    if quizPercent > 0
        for i = 1:max(target)
            idx = find(target==i);
            if length(idx)>1
                sampQuizNum(i) = round(length(idx)*quizPercent/100,0);
                samplesIdx = randperm(length(idx),sampQuizNum(i));
                samples = idx(samplesIdx);
                sampleQuizPercent(i) = (length(samples)/length(idx))*100;
            else
                samples = [ ];
                sampleQuizPercent(i) = 0;
            end
            quizSamples = [quizSamples samples];
        end
        quizNum = length(quizSamples); % total number of quiz samples
        quizInput = input(:,quizSamples); % sample inputs for quizzing
        quizTarget = target(:,quizSamples)'; % sample targets for quizzing
        storedQuizTarget = [storedQuizTarget full(ind2vec(quizTarget',max(classes)))];
        % eliminate quiz samples from input and target used for training
        trainInput=input(:,setdiff([1:length(target(1,:))],quizSamples));
        trainTarget=target(:,setdiff([1:length(target(1,:))], quizSamples));
%       sampleQuizPercent % percentage of each classification for quiz
    end
    % create and train the network
    hiddenLayerSize = [10 10];
    net = patternnet(hiddenLayerSize);
    net.divideParam.trainRatio = 0.9;
    net.divideParam.valRatio = 0.1;
    net.divideParam.testRatio = 0;
    net.trainParam.showWindow = false;
    [net,tr] = train(net,trainInput,full(ind2vec(trainTarget)));
    % validate the network
    if quizPercent > 0
        quizOutput = full(vec2ind(net(quizInput)))';
        storedQuizOutput = [storedQuizOutput full(ind2vec(quizOutput',max(classes)))];
%       quizTarget(:,z) = quizTarget(z,:)';
        error = gsubtract(quizTarget,quizOutput);
%       performance = perform(net,target, output);
        [quizTarget quizOutput]
        numCorrect = 0;
        for i = 1:quizNum
            if quizOutput(i)==quizTarget(i)
                correct(quizTarget(i),z) = correct(quizTarget(i),z) + 1;
                numCorrect = numCorrect + 1;
            end
        end
        percentCorrect(z) = (numCorrect/quizNum)*100;
%       figure,plotconfusion(full(ind2vec(quizTarget')),full(ind2vec(quizOutput')))
    end
    trainNum = length(trainTarget);
    % sample count
    sampleClasses = rawTarget;
    trainClasses = trainTarget;
    for i = 1:possibleClasses
        sampleCounter(i) = length(find(sampleClasses==i))
        trainCounter(i,z) = length(find(trainClasses==i));
        quizCounter(i,z) = length(find(quizTarget==i));
    end
    incorrect(:,z) = quizCounter(:,z) − correct(:,z);
    % various network performance outputs
    houseOutputs = net(input);
    trOut = houseOutputs(tr.trainInd);
    vOut = houseOutputs(tr.valInd);
    tsOut = houseOutputs(tr.testInd);
    trTarg = target(tr.trainInd);
    vTarg = target(tr.valInd);
    tsTarg = target(tr.testInd);
    % save network
    % save('DEtoUSCSnet_fine','net','tr')
```

```
        if length(ERvals)==length(NANDvals)
            counter = counter+1
        end
    end
end
meanTrainCounter = mean(trainCounter,2);
meanQuizCounter = mean(quizCounter,2);
meanIncorrect = mean(incorrect,2);
meanCorrect = mean(correct,2);
if ERvals(k)==ERplotval && length(ERvals)==1
    % figures of sample class distribution
    RawSCDist = figure;
    bar(classes,sampleCounter)
    hold on
    set(gca,'xtick',classes)
    axis([0 max(classes)+1 0 max(sampleCounter)])
    xlabel('Classification Number')
    ylabel('Number of Samples')
    strNUM = sprintf('Sample Classification Distribution (%i Samples)',inputNum);
    title(strNUM)
    if printval == 1
    saveas(RawSCDist,'RawSampleClassificationDistribution.jpg')
    print('RawSampleClassificationDistribution','-depsc','-tiff')
    print('RawSampleClassificationDistribution','-dtiffn','-r300')
end
hold off
NoisySCDist = figure;
bar(classes, [mean TrainCounter meanQuizCounter],'stacked')
hold on
set(gca,'xtick', classes)
axis([0 max(classes)+1 0 max(meanTrainCounter+meanQuizCounter)])
xlabel('Classification Number')
ylabel('Number of Samples')
strNUM = sprintf('Sample Classification Distribution (%i Samples)',length(trainClasses));
title(strNUM)
legend('Training Samples','Validation Samples')
if printval == 1
    saveas(NoisySCDist,'NoisySampleClassificationDistribution.jpg')
    print('NoisySampleClassificationDistribution','-depsc','-tiff')
    print('NoisySampleClassificationDistribution','-dtiffn','-r300')
end
hold off
QuizResults = figure;
bar(classes,[meanCorrect meanIncorrect],'stacked')
hold on
set(gca,'xtick', classes)
axis([0 max(classes)+1 0 max(meanCorrect+meanIncorrect)])
xlabel('Classification Number')
ylabel('Number of Samples')
strNUM = sprintf('Validation Results by Classification (%i Samples)',quizNum);
title(strNUM)
legend('Correct','Incorrect')
saveas(QuizResults,'QuizResults.jpg')
hold off
ClassAccuracy = figure;
bar(classes,(meanCorrect./meanQuizCounter)*100)
hold on
set(gca,'xtick',classes)
axis([0 max(classes)+1 0 100])
xlabel('Classification Number')
ylabel('Mean Network Accuracy (%)')
strNUM = sprintf('Accuracy by Classification (%i Samples)',quizNum);
title(strNUM)
if printval == 1
    saveas(ClassAccuracy,'ClassAccuracy.jpg')
end
hold off
% cumulative summation of percent distribution for each class
cumsum(sort(meanTrainCounter,'descend'))/trainNum*100
plotperf(tr)
figure
plotregression(trTarg,trOut,'Train',vTarg,vOut,'Validation',...
tsTarg,tsOut,'Testing')
    figure
    plotconfusion(full(ind2vec(target)), houseOutputs)
figure
plotconfusion(storedQuizTarget,storedQuizOutput)
end
% network performance output from quizzing
```

```
percentCorrect
meanPerf(k,QUAL) = mean(percentCorrect)
stdDevPerf(k,QUAL) = std(percentCorrect,1)
storedQuizTargetInd = full(vec2ind(storedQuizTarget));
storedQuizOutputInd = full(vec2ind(storedQuizOutput));
simpCONF = zeros(possibleClasses,possibleClasses);
for i = 1:length(storedQuizTargetInd)
    simpCONF(storedQuizOutputInd(i),storedQuizTargetInd(i)) =
simpCONF(storedQuizOutputInd(i),storedQuizTargetInd(i)) + 1;
end
S = sum(simpCONF)
for i = 1:possibleClasses
    for j = 1:possibleClasses
        simpCONF(i,j) = (simpCONF(i,j)/S(j)); % multiply by 100 to get percent
    end
end
% SNRvals(k)
ERvals(k)
end
end
% plot ER vs. mean performance
if length(ERvals)>length(NANDvals)
%       [ERvals' meanPerf stdDevPerf]
    ERplot = figure;
%       strColor = ['b','r','g','m'];
for i = 1:length(qualnum)
    e=errorbar(ERvals,meanPerf(:,i),stdDevPerf(:,i),'linewidth',1.5);
%       e.Color = strColor(i);
    hold on
    end
    axis([min(ERvals) max(ERvals) 50 100])
    xlabel('Added Percent Error Threshold (%)')
    ylabel('Mean Network Accuracy (%)')
    title({'Network Performance vs. ER';'(100 Networks)'} )
    legend('No Qualitative Noise','Qualitative Noise - 1 Test',...
        'Qualitative Noise - 2 Tests','Qualitative Noise - 3 Tests',...
        'location','best')
    if printval == 1
        saveas(ERplot,'PERFvsER.jpg')
        print('PERFvsER','-depsc','-tiff')
        print('PERFvsER','-dtiffn','-r300')
    end
end
```

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] E. Adam, A. Agib, Compressed Stabilised Earth Block Manufacture in Sudan, Paris, France, 2001. http://unesdoc.unesco.org/images/0012/001282/128236e.pdf.

[2] G. T. R. Allen, Strength Properties of Stabilized Compressed Earth Blocks with Varying Soil Compositions, University of Colorado, Boulder, 2012. http://0-search.proquest.com.fama.us.es/docview/1112064607?accountid=14744.

[3] M. Bachar, L. Azzouz, M. Rabehi, B. Mezghiche, Characterization of a stabilized earth concrete and the effect of incorporation of aggregates of cork on its thermo-mechanical properties: Experimental study and modeling, Constr. Build. Mater. 74 (2015) 259-267. http://dx.doi.org/10.1016/j.conbuildmat.2014.09.106.

[4] J. Dahmen, J. F. Muñoz, Earth masonry unit: sustainable CMU alternative, Int. J. GEOMATE. 6 (2014) 903-909.

[5] B. R. Grunert, The development of a standard of care defining suitable testing of geomaterials intended for unstabilized compressed earth block construction, University of Colorado, Boulder, 2009. http://0-search.proquest.comfama.us.es/docview/304860981?accountid=14744.

[6] H. Guillaud, T. Joffroy, P. Odul, Compressed Earth Blocks: Manual of Design and Construction, Vieweg, Eschborn, Germany, 1995.

[7] M. C. Jiménez Delgado, I. C. Guerrero, The selection of soils for unstabilised earth building: A normative review, Constr. Build. Mater. 21 (2007) 237-251.

[8] G. Minke, Building with Earth: Design and Technology of a Sustainable Architecture, 2nd ed., Birkhaeuser, Basel, Switzerland, 2006.

[9] J. J. Morony, Adobe Moisture Absorption and Temperature Control, Uvalde, Tex., 2005.

[10] V. Rigassi, Compressed Earth Blocks: Manual of Production, Vieweg, Eschborn, Germany, 1985.

[11] F. V. Riza, I. A. Rahman, A. M. A. Zaidi, A brief review of Compressed Stabilized Earth Brick (CSEB), in: CSSR 2010-2010 Int. Conf. Sci. Soc. Res., Institute of Electrical and Electronics Engineers, 2010: pp. 999-1004.

[12] A. D. Krosnowski, A Proposed Best Practice Method of Defining a Standard of Care for Stabilized Compressed Earthen Block Production, University of Colorado, Boulder, 2011. http://0-search.proquest.com.fama.us.es/docview/897131638?accountid=14744.

[13] C. Egenti, J. M. Khatib, D. Oloke, Conceptualisation and pilot study of shelled compressed earth block for sustainable housing in Nigeria, Int. J. Sustain. Built Environ. 3 (2014) 72-86.

[14] J. C. Morel, A. Pkla, P. Walker, Compressive strength testing of compressed earth blocks, Constr. Build. Mater. 21 (2007) 303-309.

[15] J. E. Aubert, A. Marcom, P. Oliva, P. Segui, Chequered earth construction in south-western France, J. Cult. Herit. 16 (2015) 293-298.

[16] ASTM, Standard Test Method for Particle-Size Analysis of Soil, American Society for Testing and Materials, West Conshohocken, Pa., 2007.

[17] ASTM, Standard Test Methods for Liquid Limit, Plastic Limit, and Plasticity Index of Soils, American Society for Testing and Materials, West Conshohocken, Pa., 2010.

[18] ASTM, Standard Practice for Classification of Soils for Engineering Purposes (Unified Soil Classification System), American Society for Testing and Materials, West Conshohocken, Pa., 2011.

[19] M. I. Kaniu, K. H. Angeyo, Challenges in rapid soil quality assessment and opportunities presented by multivariate chemometric energy dispersive X-ray fluorescence and scattering spectroscopy, Geoderma. 241-242 (2015) 32-40. http://dx.doi.org/10.1016/j.geoderma.2014.10.014.

[20] B. A. Story, G. T. Fry, Methodology for Designing Diagnostic Data Streams for Use in a Structural Impairment Detection System, J. Bridg. Eng. 19 (2014). http://ascelibrary.org/doi/10.1061/%28ASCE%29BE.1943-5592.0000556.

[21] B. A. Story, G. T. Fry, A Structural Impairment Detection System Using Competitive Arrays of Artificial Neural Networks, Comput. Civ. Infrastruct. Eng. 29 (2014) 180-190. http://doi.wiley.com/10.1111/mice.12040 (accessed Sep. 15, 2016).

[22] Y. Zeinali, B. A. Story, Structural Impairment Detection Using Deep Counter Propagation Neural Networks, in: Int. Conf. Sustain. Des. Eng. Constr., Procedia Engineering, Tempe, Ariz., 2016: pp. 868-875. http://linkinghub.elsevier.com/retrieve/pii/S1877705816301199 (accessed Sep. 15, 2016).

[23] S. Haykin, Neural Networks: A Comprehensive Foundation, Macmillan College
Publishing Company, Englewood Cliffs, N.J., 1994.

[24] M. T. Hagan, H. B. Demuth, M. H. Beale, O. De JesUs, Neural Network Design, 2nd ed., Pws Pub., Boston, Mass., 1997.

[25] H. Adeli, Neural networks in civil engineering: 1989-2000, Comput. Civ. Infrastruct. Eng. 16 (2001) 126-142. doi:10.1111/0885-9507.00219.

[26] Y. Zeinali, B. A. Story, Competitive probabilistic neural network, Integr. Comput. Aided. Eng. Preprint (2017) 1-14.

[27] P. Bhargavi, S. Jyothi, Applying Naive Bayes data mining technique for classification of agricultural land soils, Int. J. Comput. Sci. Netw. Secur. 9 (2009) 117-122. http://paper.ijcsns.org/07_book/200908/20090817.pdf.

[28] P. Bhargavi, S. Jyothi, Soil Classification Using Gatree, Int. J. Comput. Sci. Inf. Technol. 2 (2010) 184-191.

[29] K. Hornik, M. Stinchcombe, H. White, Multilayer Feedforward Networks are Universal Approximators, Neural Networks. 2 (1989) 359-366. doi:0893-6080/89.

[30] DwellEarth Inc., www.DwellEarth.com, (2016). https://dwellearth.com/soil-science-2/.

What is claimed is:

1. A method of determining a soil classification for selecting a soil additive comprising:
   obtaining a soil sample;
   conducting two or more field tests on the soil sample to determine percent gravel, percent fines, and the plasticity index to obtain raw data for each of the two or more field tests, wherein at least one test is qualitative and one test if quantitative, wherein the qualitative field test is selected from at least one of pen, stick, and shine tests, and the quantitative test is selected from at least one of a wash test, a feel test, a test tube particle graduation, or a jar test;
   using a processor to train a neural network using at least two hidden layers to obtain a validation dataset that is applied to the soil sample tests of both quantitative and qualitative datasets; and
   calculating the soil classification from the raw data by applying the validation dataset obtained from a training and validation soil classification calculation of both quantitative and qualitative datasets using samples of known soil classification, wherein the validation dataset is obtained using a feed-forward backpropagation neural network, wherein the training occurs by adjustment of one or more synaptic weights, wherein the one or more synaptic weights are initialized as random numbers in a first pass of a training dataset that are input into the feed-forward backpropagation neural network and an output is generated, if this output does not match a target output within a predefined acceptable error, the weights and biases within the feed-forward backpropagation neural network are adjusted by reducing an error function related to a simulated output and the target output; and
   wherein the soil classification is within 10% of a known soil classification obtained using laboratory testing of a soil having any known soil classification;
   wherein the soil classification is used for selecting the soil additive used to prepare a mix for making a compressed earth block brick of a desired brick strength.

2. The method of claim 1, wherein the soil classification is determined without laboratory equipment.

3. The method of claim 1, further comprising the step of displaying graphically the soil classification.

4. The method of claim 1, wherein the soil classification is a Unified Soil Classification System (USCS) classification.

5. The method of claim 1, further comprising displaying the soil classification on a soil texture triangle.

6. The method of claim 1, further comprising adding noise to the test samples that comprise one or more qualitative tests used to train a neural network to obtain the validation dataset that is applied to the tests of the soil samples.

7. A system for determining a soil classification for selecting a soil additive comprising:
   a processor comprising a non-transitory computer readable medium comprising instructions stored thereon for:
   obtaining a soil sample;
   conducting two or more field tests on the soil sample to determine percent gravel, percent fines, and the plasticity index to obtain raw data for each of the two or more field tests, wherein at least one test is qualitative and one test if quantitative, wherein the qualitative field test is selected from at least one of pen, stick, and shine tests, and the quantitative test is selected from at least one of a wash test, a feel test, a test tube particle graduation, or a jar test;
   using a processor to train a neural network using at least two hidden layers to obtain a validation dataset that is applied to the soil sample tests of both quantitative and qualitative datasets; and
   calculating the soil classification from the raw data by applying the validation dataset obtained from a training and validation soil classification calculation of both quantitative and qualitative datasets using samples of known soil classification, wherein the validation dataset is obtained using a feed-forward backpropagation neural network, wherein the training occurs by adjustment of one or more synaptic weights, wherein the one or more synaptic weights are initialized as random numbers in a first pass of a training dataset that are input into the feed-forward backpropagation neural network and an output is generated, if this output does not match a target output within a predefined acceptable error, the weights and biases within the feed-forward backpropagation neural network are adjusted by reducing an error function related to a simulated output and the target output; and
   wherein the soil classification is within 10% of a known soil classification obtained using laboratory testing of a soil having any known soil classification;
   wherein the soil classification is used for selecting the soil additive used to prepare a mix for making a compressed earth block brick of a desired brick strength.

8. The system of claim 7, wherein the soil classification is determined without laboratory equipment.

9. The system of claim 7, further comprising the step of displaying graphically the soil classification.

10. The system of claim 7, wherein the soil classification is a Unified Soil Classification System (USCS) classification.

11. The system of claim 7, further comprising displaying the soil classification on a soil texture triangle.

12. The system of claim 7, further comprising adding noise to the test samples that comprise one or more qualitative tests used to train a neural network to obtain the validation dataset that is applied to the tests of the soil samples.

* * * * *